United States Patent
Weichert et al.

(10) Patent No.: US 10,813,998 B2
(45) Date of Patent: *Oct. 27, 2020

(54) LONG-LIVED GADOLINIUM BASED TUMOR TARGETING IMAGING AND THERAPY AGENTS

(71) Applicant: Wisconsin Alumni Research Foundation, Madison, WI (US)

(72) Inventors: Jamey Weichert, Sun Prairie, WI (US); Anatoly Pinchuk, Fitchburg, WI (US); Wolfgang Axel Tome, Ardsley, NY (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/285,358

(22) Filed: Feb. 26, 2019

(65) Prior Publication Data

US 2019/0184014 A1 Jun. 20, 2019

Related U.S. Application Data

(63) Continuation of application No. 15/343,580, filed on Nov. 4, 2016, now Pat. No. 10,265,398.

(60) Provisional application No. 62/252,218, filed on Nov. 6, 2015.

(51) Int. Cl.
| | | |
|---|---|---|
| *A61K 41/00* | (2020.01) | |
| *A61K 49/10* | (2006.01) | |
| *A61K 51/04* | (2006.01) | |
| *A61K 49/08* | (2006.01) | |
| *G01N 33/574* | (2006.01) | |
| *G01N 33/58* | (2006.01) | |
| *C07F 9/6515* | (2006.01) | |
| *C07F 9/6524* | (2006.01) | |
| *C07F 9/6561* | (2006.01) | |
| *C07F 9/09* | (2006.01) | |
| *C07F 9/11* | (2006.01) | |
| *A61N 5/10* | (2006.01) | |
| *C07F 9/10* | (2006.01) | |
| *G01N 33/60* | (2006.01) | |
| *A61K 39/00* | (2006.01) | |

(52) U.S. Cl.
CPC .......... *A61K 41/009* (2013.01); *A61K 49/085* (2013.01); *A61K 49/10* (2013.01); *A61K 49/106* (2013.01); *A61K 51/0482* (2013.01); *A61N 5/1039* (2013.01); *A61N 5/1048* (2013.01); *A61N 5/1077* (2013.01); *C07F 9/091* (2013.01); *C07F 9/10* (2013.01); *C07F 9/11* (2013.01); *C07F 9/6515* (2013.01); *C07F 9/6524* (2013.01); *C07F 9/6561* (2013.01); *G01N 33/574* (2013.01); *G01N 33/58* (2013.01); *G01N 33/60* (2013.01); *A61K 2039/505* (2013.01); *A61N 2005/109* (2013.01); *G01N 2458/15* (2013.01)

(58) Field of Classification Search
CPC ......... A61K 41/00; A61K 49/10; A61K 51/04
See application file for complete search history.

*Primary Examiner* — Michael G. Hartley
*Assistant Examiner* — Jagadishwar R Samala
(74) *Attorney, Agent, or Firm* — Boyle Fredrickson S.C.

(57) ABSTRACT

Alkylphosphocholine analogs incorporating a chelating moiety that is chelated to gadolinium are disclosed herein. The alkylphophocholine analogs are compounds having the formula:

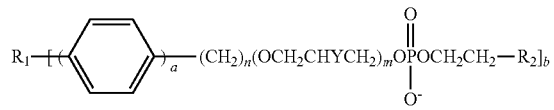

or a salt thereof. $R_1$ includes a chelating agent that is chelated to a gadolinium atom; a is 0 or 1; n is an integer from 12 to 30; m is 0 or 1; Y is —H, —OH, —COOH, —COOX, —OCOX, or —OX, wherein X is an alkyl or an arylalkyl; $R_2$ is —$N^+H_3$, —$N^+H_2Z$, —$N^+HZ_2$, or —$N^+Z_3$, wherein each Z is independently an alkyl or an aroalkyl; and b is 1 or 2. The compounds can be used to detect solid tumors or to treat solid tumors. In detection/imaging applications, the gadolinium emits signals that are detectable using magnetic resonance imaging. In therapeutic treatment, the gadolinium emits tumor-targeting charged particles when exposed to epithermal neutrons.

5 Claims, 20 Drawing Sheets

LONG-LIVED GADOLINIUM BASED TUMOR TARGETING IMAGING AND THERAPY AGENTS

CROSS-REFERENCE TO RELATED APPLICATIONS

This application is a continuation of U.S. application Ser. No. 15/343,580 filed on Nov. 4, 2016, which claims the benefit of U.S. provisional Application No. 62/252,218 filed on Nov. 6, 2015. Each of these applications is incorporated by reference herein in its entirety.

STATEMENT REGARDING FEDERALLY SPONSORED RESEARCH OR DEVELOPMENT

Not applicable.

FIELD OF THE DISCLOSURE

This disclosure relates generally to disease treatment and medical diagnosis/imaging. In particular, the disclosure is directed to (a) gadolinium-containing alkylphosphocholine analogs, (b) methods of detecting/imaging tumor cells using such compounds, and (c) related radiotherapy methods.

BACKGROUND

We have previously shown that certain alkylphosphocholine analogs are preferentially taken up and retained by malignant solid tumor (i.e., solid tumor cancer) cells. In U.S. Patent Publication No. 2014/0030187, which is incorporated by reference herein in its entirety, Weichert et al. disclose using analogs of the base compound 18-(p-iodophenyl) octadecyl phosphocholine (NM404; see FIG. 1) for detecting and locating, as well as for treating, a wide variety of solid tumor cancers. For example, if the iodo moiety is an imaging-optimized radionuclide, such as iodine-124 ([$^{124}$I]-NM404), the analog can be used in positron emission tomography-computed tomography (PET/CT) or single-photon emission computed tomography (SPECT) imaging of adult solid tumors. Alternatively, if the iodo moiety is a radionuclide optimized for delivering therapeutic doses of radiation to the solid tumors cells in which the analog is taken up, such as iodine-125 or iodine-131 ([$^{125}$I]-NM404 or [$^{131}$I]-NM404), the analog can be used to treat solid tumors.

However, there are currently no long-lived computerized tomography (CT) or magnetic resonance (MR) imaging agents that have been shown to successfully target tumor cells in vivo. Non-specific short-lived agents in both modalities are used for cancer imaging by contrasting normal organ tissues while in the process of renal or hepatobiliary excretion. There are currently a variety of radiopharmaceuticals available for tumor imaging, but these are limited by non-specificity for malignancy, the inability to distinguish cancer from inflammation, short biological half-life, and generally poor spatial resolution associated with PET and SPECT scanning modalities.

Accordingly, there is a need in the art for a tumor-specific agent for use in MR scanning, CT scanning, or in both imaging methods. Such a tumor-specific agent for MR or CT scanning would represent at least a ten-fold improvement in the spatial resolution currently attainable with positron emission agents and PET scanning.

BRIEF SUMMARY

The current disclosure provides new gadolinium (Gd)-labeled phospholipid compounds that can be used long-lived tumor-specific MR imaging agents and as neutron capture therapy agents.

The phospholipid metal chelate compounds disclosed herein utilize an alkylphospholipid carrier combined with one of a variety of metal chelators that is chelated to a gadolinium atom. The disclosed metal chelates are preferentially taken up by malignant solid tumor cells, as compared to non-tumor cells. Preferential uptake of such compounds renders them suitable for use as Gd-containing MR contrast/imaging agents that can be used in malignant solid tumor detection/imaging applications. Furthermore, the compounds can be used in therapeutic treatment, either by using the MR imaging results obtained using the compounds as contrast agents for targeting external beam readiation to one or more solid tumors, or by using the compounds to facilitate neutron capture therapy against the tumors.

In a first aspect, the disclosure encompasses a compound having the formula:

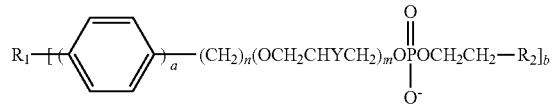

or a salt thereof. $R_1$ includes or is a chelating agent that is chelated to one or more gadolinium atoms; a is 0 or 1; n is an integer from 12 to 30; m is 0 or 1; Y is —H, —OH, —COOH, —COOX, —OCOX, or —OX, wherein X is an alkyl or an arylalkyl; $R_2$ is —N$^+$H$_3$, —N$^+$H$_2$Z, —N$^+$HZ$_2$, or —N$^+$Z$_3$, wherein each Z is independently an alkyl or an aroalkyl; and b is 1 or 2.

In some embodiments, the one or more gadolinium atoms are in the form of a Gd(III) cation.

In some embodiments, the metal atom is an alpha, beta or Auger emitting metal isotope with a half life of greater than 6 hours and less than 30 days. Such isotopes are particularly suited for use in targeted radiotherapy applications. Non-limiting examples of such isotopes include Lu-177, Y-90, Ho-166, Re-186, Re-188, Cu-67, Au-199, Rh-105, Ra-223, Ac-225, As-211, Pb-212, and Th-227.

In some embodiments, the chelating agent is 1,4,7,10-tetraazacyclododecane-1,4,7-triacetic acid (DO3A) or one of its derivatives; 1,4,7-triazacyclononane-1,4-diacetic acid (NODA) or one of its derivatives; 1,4,7-triazacyclononane-1,4,7-triacetic acid (NOTA) or one of its derivatives; 1,4,7,10-tetraazacyclododecane-1,4,7,10-tetraacetic acid (DOTA) or one of its derivatives; 1,4,7-triazacyclononane, 1-glutaric acid-4,7-diacetic acid (NODAGA) or one of its derivatives; 1,4,7,10-tetraazacyclodecane, 1-glutaric acid-4,7,10-triacetic acid (DOTAGA) or one of its derivatives; 1,4,8,11-tetraazacyclotetradecane-1,4,8,11-tetraacetic acid (TETA) or one of its derivatives; 1,4,8,11-tetraazabicyclo[6.6.2] hexadecane-4,11-diacetic acid (CB-TE2A) or one of its derivatives; diethylene triamine pentaacetic acid (DTPA), its diester, or one of its derivatives; 2-cyclohexyl diethylene triamine pentaacetic acid (CHX-A"-DTPA) or one of its derivatives; deforoxamine (DFO) or one of its derivatives; 1,2-[[6-carboxypyridin-2-yl]methylamino]ethane (H₂dedpa) or one of its derivatives; or DADA or one of its derivatives, wherein DADA has the structure:

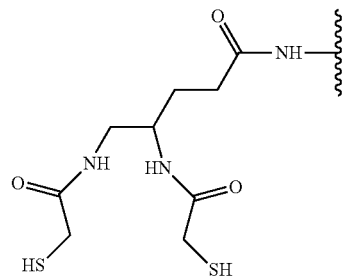 [SMILES: *NC(=O)CCC(CNC(=O)CS)NC(=O)CS]

In some embodiments, a is 1 (aliphatic aryl-alkyl chain). In other embodiments, a is 0 (aliphatic alkyl chain).

In some embodiments, m is 1 (acylphospholipid series).

In some embodiments, n is an integer between 12 and 20.

In some embodiments, Y is —OCOX, —COOX or —OX. In some such embodiments, X is —CH₂CH₃ or —CH₃.

In some embodiments, m is 0 (alkylphospholipid series).

In some embodiments, b is 1.

In some embodiments, n is 18.

In some embodiments, $R_2$ is —N⁺Z₃. In some such embodiments, each Z is independently —CH₂CH₃ or —CH₃. In some such embodiments, each Z is —CH₃.

Non-limiting examples of the chelating agent that can be chelated to the metal atom include:

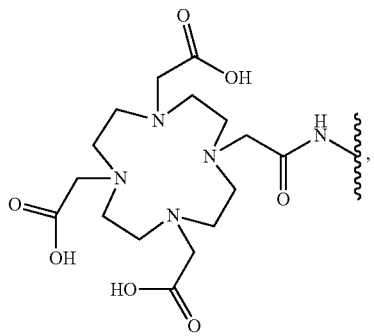

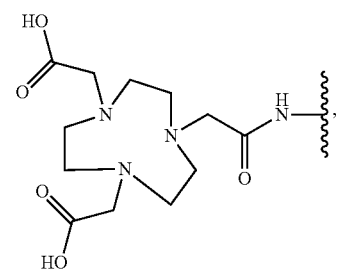

-continued

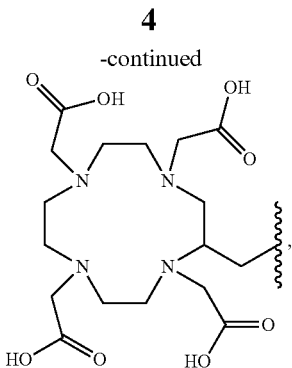

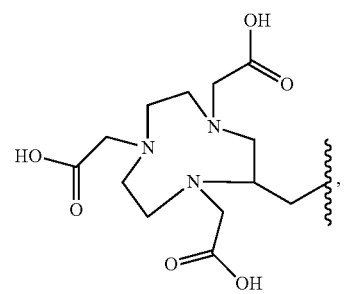

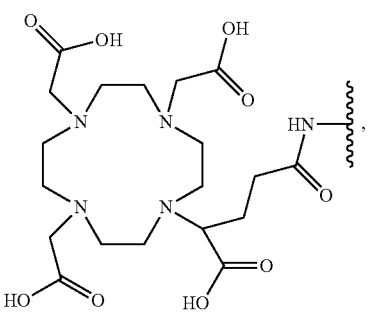

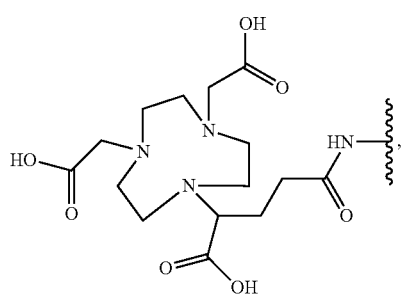

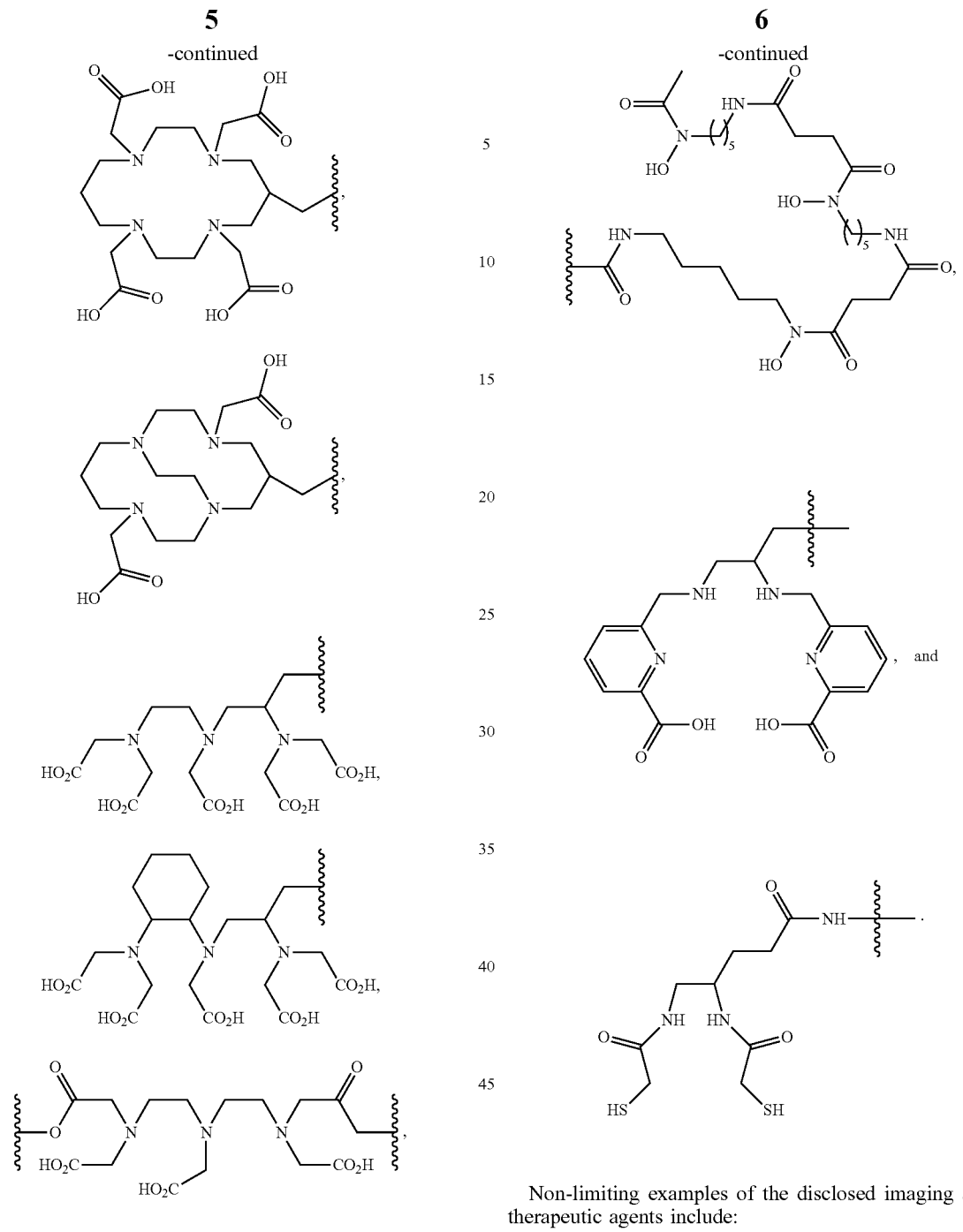
Non-limiting examples of the disclosed imaging and/or therapeutic agents include:
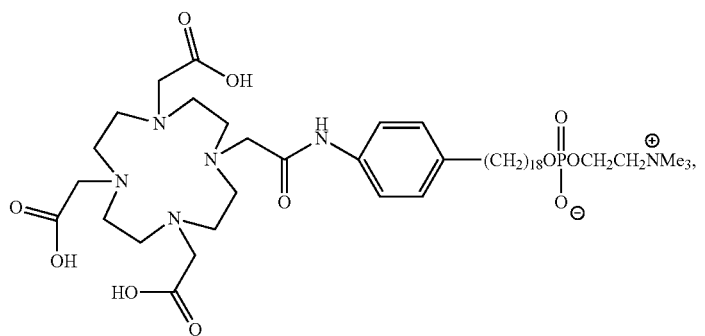

-continued
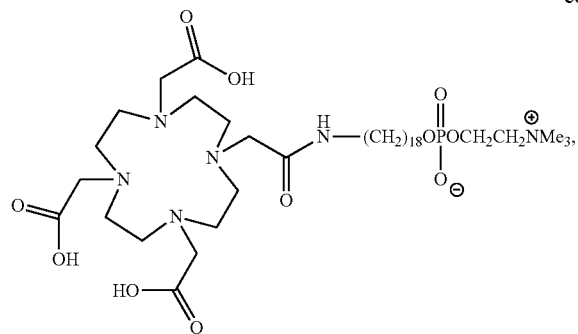
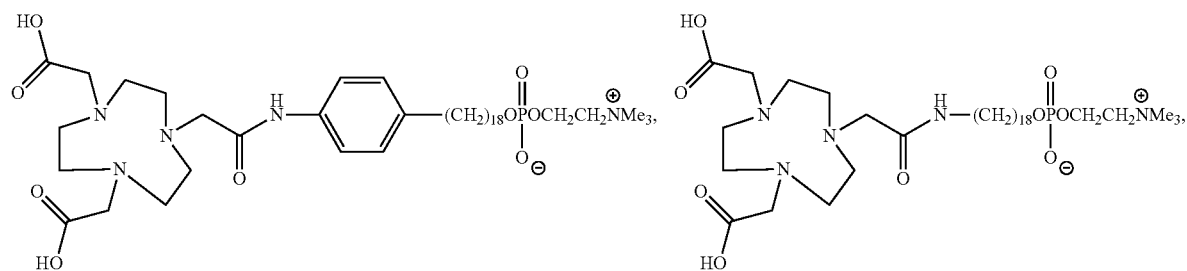
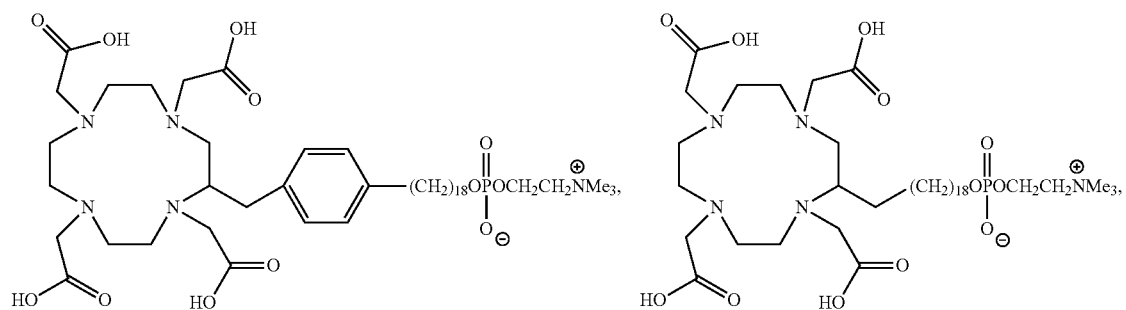
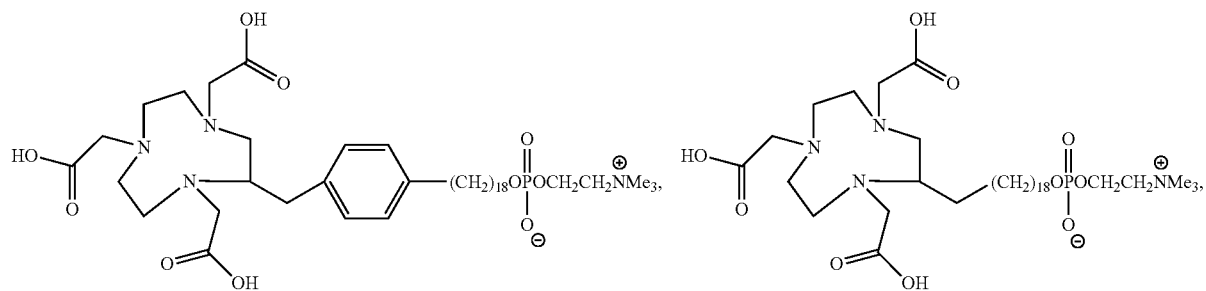
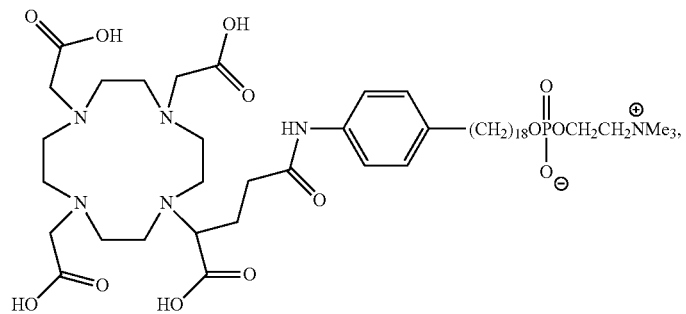

-continued
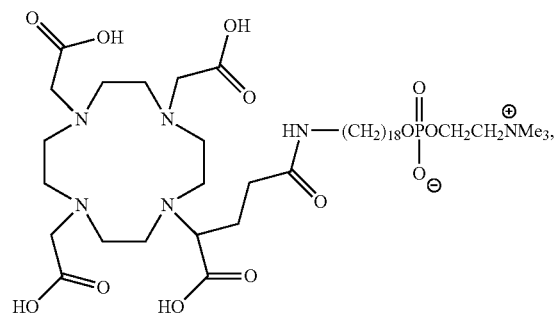
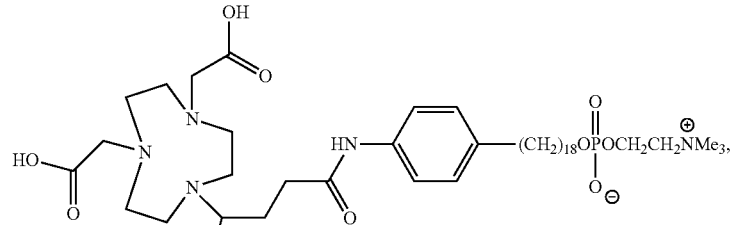
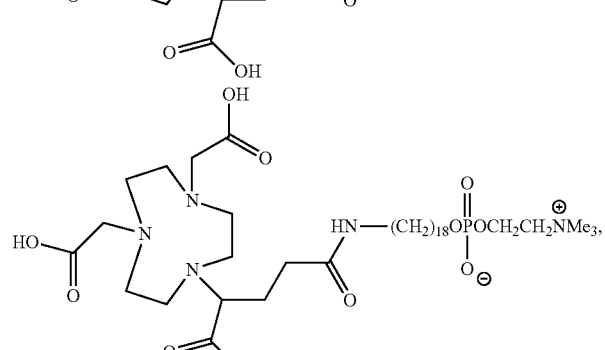
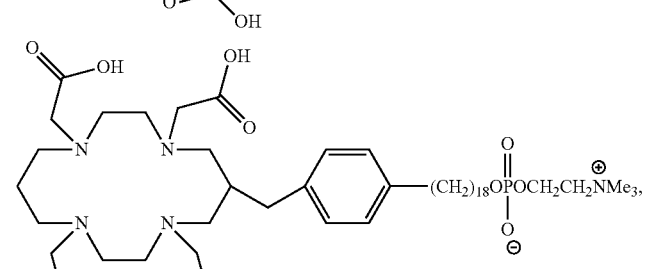
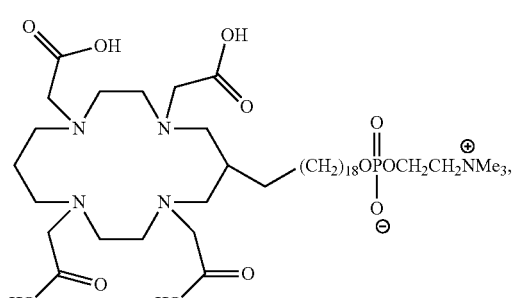
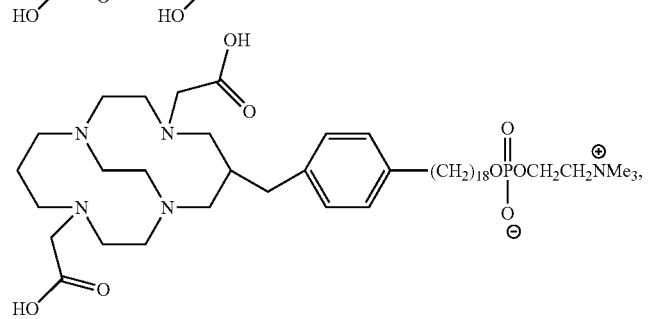
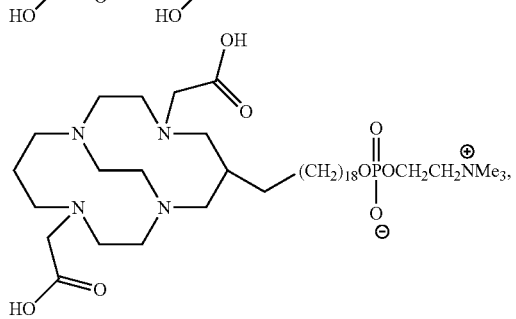
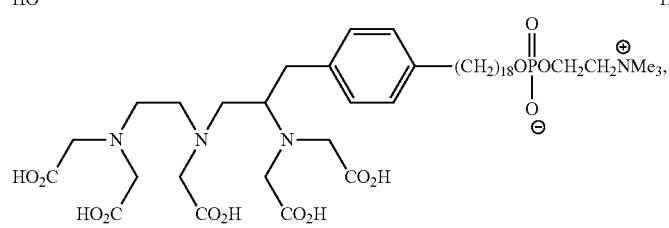
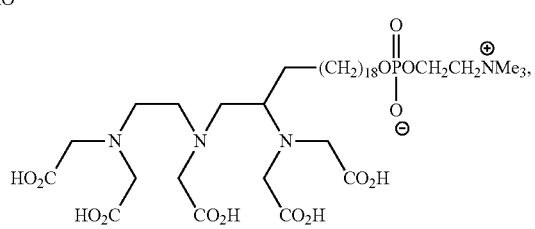

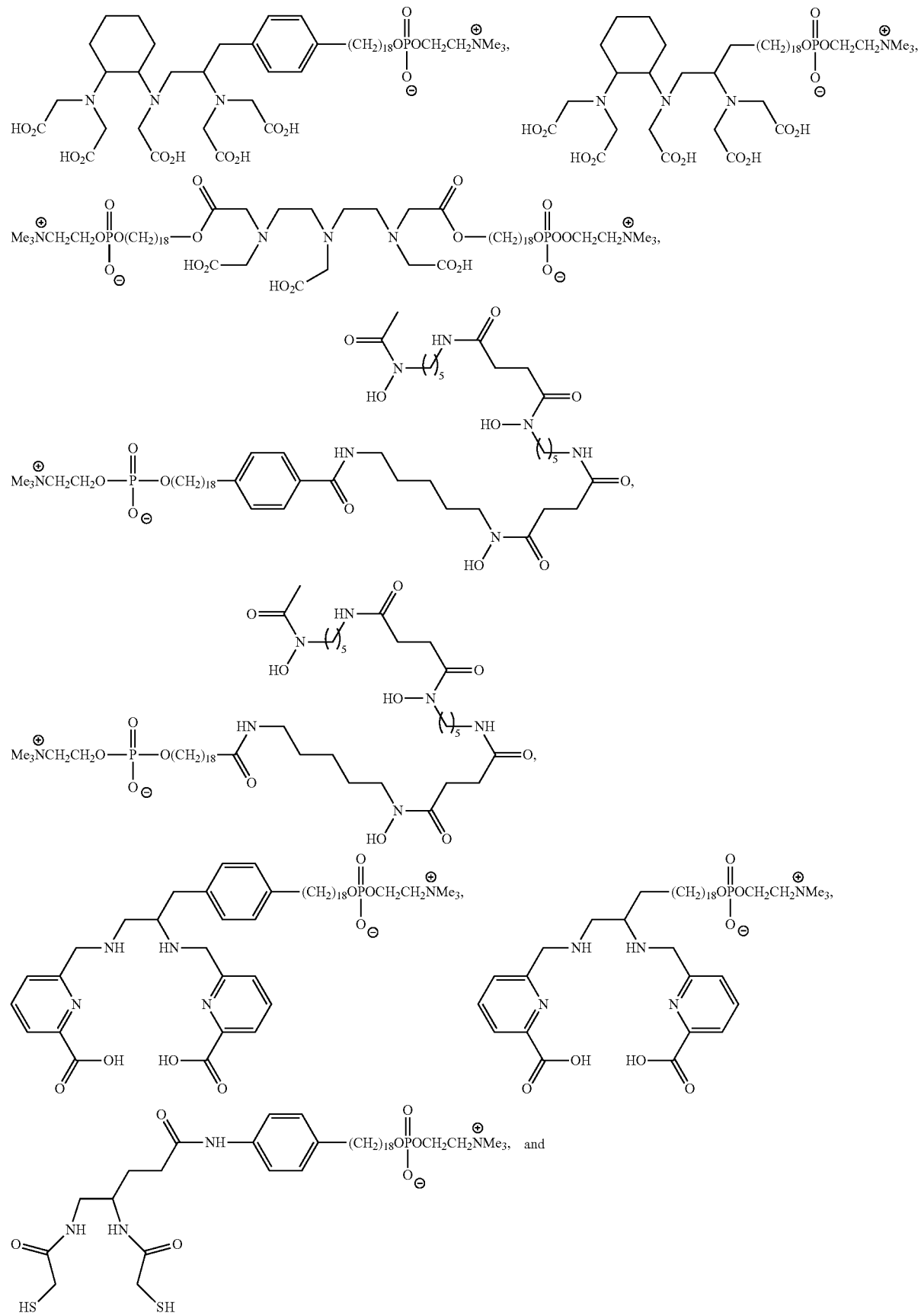

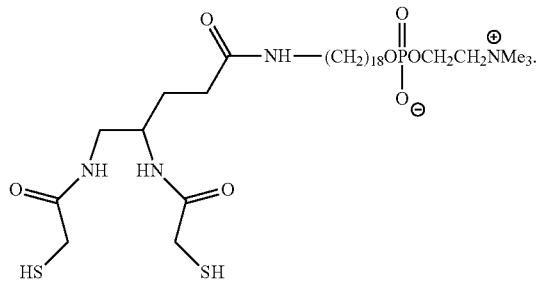

In each case, the exemplary compound is chelated to one or more gadolinium atoms.

In some embodiments, the compound is:

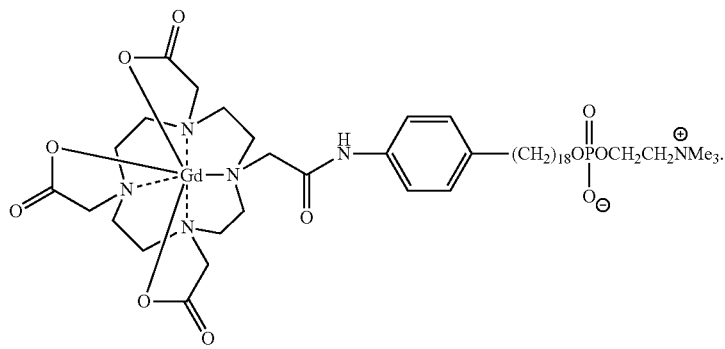

(Gd-DO3A-404)

In a second aspect, the disclosure encompasses a composition that includes one or of the compounds described above, and a pharmaceutically acceptable carrier.

In a third aspect, the disclosure encompasses one or more of the compounds described above for use in magnetic resonance imaging of cancer or cancerous cells.

In a fourth aspect, the disclosure encompasses one or more of the compounds described above for use in treating cancer by neutron capture therapy.

In a fifth aspect, the disclosure encompasses one or more of the compounds described above for use in manufacturing a medicament for treating or imaging cancer.

In a sixth aspect, the disclosure encompasses a method for detecting or imaging one or more cancer tumor cells in a biological sample. The method includes the steps of (a) contacting the biological sample with one or more of the compounds described above, whereby the compound is differentially taken up by malignant solid tumor cells within the biological sample; and (b) identifying individual cells or regions within the biological sample that are emitting signals characteristic of gadolinium.

In some embodiments, the step of identifying individual cells or regions within the biological sample that are emitting signals characteristic of gadolinium is performed by magnetic resonance imaging (MRI).

In some embodiments, the biological sample is part or all of a subject.

In some embodiments, the biological sample is obtained from a subject.

In some embodiments, the subject is a human.

In some embodiments, the cancer cells are adult solid tumor cells or pediatric solid tumor cells. Non-limiting examples of such cells include melanoma cells, neuroblastoma cells, lung cancer cells, adrenal cancer cells, colon cancer cells, colorectal cancer cells, ovarian cancer cells, prostate cancer cells, liver cancer cells, subcutaneous cancer cells, squamous cell cancer cells, intestinal cancer cells, retinoblastoma cells, cervical cancer cells, glioma cells, breast cancer cells, pancreatic cancer cells, Ewings sarcoma cells, rhabdomyosarcoma cells, osteosarcoma cells, retinoblastoma cells, Wilms' tumor cells, and pediatric brain tumor cells.

In a seventh aspect, the disclosure encompasses a method of diagnosing cancer in a subject. The method includes one or more of the imaging/detection steps outlined above. In the method, the biogical sample is obtained from, part of, or all of a subject. If cancer cells are detected or imaged in the method steps, the subject is diagnosed with cancer.

In some embodiments, the cancer that is diagnosed is an adult solid tumor or a pediatric solid tumor. Non-limiting examples of such cancer include melanoma, neuroblastoma, lung cancer, adrenal cancer, colon cancer, colorectal cancer, ovarian cancer, prostate cancer, liver cancer, subcutaneous cancer, squamous cell cancer, intestinal cancer, retinoblastoma, cervical cancer, glioma, breast cancer, pancreatic cancer, Ewings sarcoma, rhabdomyosarcoma, osteosarcoma, retinoblastoma, Wilms' tumor, and pediatric brain tumors.

In an eighth aspect, the disclosure encompasses a method of monitoring the efficacy of a cancer therapy in a human subject. The method includes performing one or more of the imaging/detection steps outlined above at two or more different times on the biological sample, wherein the biogical sample is obtained from, part of, or all of a subject. The change in strength of the signals characteristic of the metal isotope between the two or more different times is correlated with the efficacy of the cancer therapy.

In some embodiments, the cancer therapy being monitored is chemotherapy or radiotherapy.

In a ninth aspect, the disclosure encompasses a method of treating cancer in a subject. The method includes performing one or more of the imaging/detection steps outlined above, wherein the biogical sample is part of or all of a subject. The method also includes the step of directing an external radiotherapy beam to the identified individual cells or regions within the subject.

In a tenth aspect, the disclosure encompasses a method for treating a cancer in a subject by neutron capture therapy. The method includes the steps of administering to a subject having cancer an effective amount of one or more of the compounds described above, and radiating the subject with epithermal neutrons. The compounds absorb the neutrons and subsequently emit high-energy charged particles to the local environment, which can effectively treat the cancer.

In some embodiments, the compound is administered by parenteral, intranasal, sublingual, rectal, or transdermal delivery. In some such embodiments, the compound is administered intravenously. In some embodiments, the compound is administered intratumoraly.

In some embodiments, the subject is a human.

In some embodiments, the cancer that is treated is an adult solid tumor or a pediatric solid tumor. Non-limiting examples of cancers that could be treated include melanoma, neuroblastoma, lung cancer, adrenal cancer, colon cancer, colorectal cancer, ovarian cancer, prostate cancer, liver cancer, subcutaneous cancer, squamous cell cancer, intestinal cancer, retinoblastoma, cervical cancer, glioma, breast cancer, pancreatic cancer, Ewings sarcoma, rhabdomyosarcoma, osteosarcoma, retinoblastoma, Wilms' tumor, and pediatric brain tumors.

Other objects, features and advantages of the present invention will become apparent after review of the specification, claims and drawings.

BRIEF DESCRIPTION OF THE DRAWINGS

FIG. 3 (right panel) shows $R_2$ relaxation rate as a function of Gd-DO3A-404 concentration, both as $T_1$-weighted images (top right) and plotted as a graph (bottom right). The linear relationship shown by the graph defines transverse relaxivity ($r_2$).

FIG. 8 includes T1-weighted SPGR MR images obtained before the contrast agent is injected. The locations of the myocardium (M, top image), liver (L, center image), and kidney (K, bottom image) are indicated by arrows, and are consistent with the corresponding images shown in FIGS. 9-12.

FIG. 9 includes T1-weighted SPGR MR images obtained one hour after Gd-DO3A-404 contrast agent is injected. The images include the myocardium (top image), liver (center image), and kidney (bottom image).

FIG. 10 includes T1-weighted SPGR MR images obtained 24 hours after Gd-DO3A-404 contrast agent is injected. The images include the myocardium (top image), liver (center image), and kidney (bottom image).

FIG. 11 includes T1-weighted SPGR MR images obtained four days after Gd-DO3A-404 contrast agent is injected. The images include the myocardium (top image), liver (center image), and kidney (bottom image).

FIG. 12 includes T1-weighted SPGR MR images obtained seven days after Gd-DO3A-404 contrast agent is injected. The images include the myocardium (top image), liver (center image), and kidney (bottom image).

DETAILED DESCRIPTION

I. In General

Figure 1:
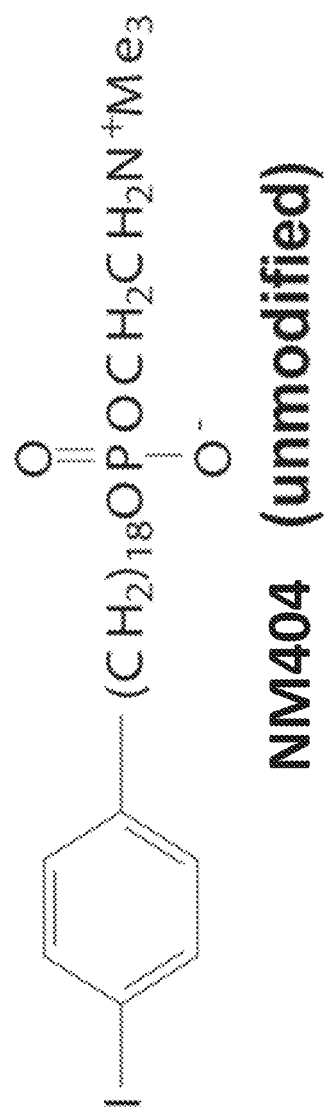
FIG. 1 shows the chemical structure of the base compound 18-(p-iodophenyl)octadecyl phosphcholine (NM404).

It is understood that this disclosure is not limited to the particular methodology, protocols, materials, and reagents described, as these may vary. The terminology used herein is for the purpose of describing particular embodiments only, and is not intended to limit the scope of the present invention, which will be limited only by any later-filed nonprovisional applications.

As used herein and in the appended claims, the singular forms "a", "an", and "the" include plural reference unless the context clearly dictates otherwise. As well, the terms "a" (or "an"), "one or more" and "at least one" can be used interchangeably herein. The terms "comprising" and variations thereof do not have a limiting meaning where these terms appear in the description and claims. Accordingly, the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art.

The terminology as set forth herein is for description of the embodiments only and should not be construed as limiting of the invention as a whole. Unless otherwise specified, "a," "an," "the," and "at least one" are used interchangeably and mean one or more than one.

The disclosure is inclusive of the compounds described herein (including intermediates) in any of their pharmaceutically acceptable forms, including isomers (e.g., diastereomers and enantiomers), tautomers, salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

"Pharmaceutically acceptable" as used herein means that the compound or composition or carrier is suitable for administration to a subject to achieve the treatments described herein, without unduly deleterious side effects in light of the necessity of the treatment.

The term "effective amount," as used herein, refers to the amount of the compounds or dosages that will elicit the biological or medical response of a subject, tissue or cell that is being sought by the researcher, veterinarian, medical doctor or other clinician.

As used herein, "pharmaceutically-acceptable carrier" includes any and all dry powder, solvents, dispersion media, coatings, antibacterial and antifungal agents, isotonic agents, absorption delaying agents, and the like. Pharmaceutically-acceptable carriers are materials, useful for the purpose of administering the compounds in the method of the present invention, which are preferably non-toxic, and may be solid, liquid, or gaseous materials, which are otherwise inert and pharmaceutically acceptable, and are compatible with the compounds of the present invention. Examples of such carriers include, without limitation, various lactose, mannitol, oils such as corn oil, buffers such as PBS, saline, polyethylene glycol, glycerin, polypropylene glycol, dimethylsulfoxide, an amide such as dimethylacetamide, a protein such as albumin, and a detergent such as Tween 80, mono- and oligopolysaccharides such as glucose, lactose, cyclodextrins and starch.

The term "administering" or "administration," as used herein, refers to providing the compound or pharmaceutical composition of the invention to a subject suffering from or at risk of the diseases or conditions to be treated or prevented.

A route of administration in pharmacology is the path by which a drug is taken into the body. Routes of administration may be generally classified by the location at which the substance is applied. Common examples may include oral and intravenous administration. Routes can also be classified based on where the target of action is. Action may be topical (local), enteral (system-wide effect, but delivered through the gastrointestinal tract), or parenteral (systemic action, but delivered by routes other than the GI tract), via lung by inhalation.

A topical administration emphasizes local effect, and substance is applied directly where its action is desired.

Sometimes, however, the term topical may be defined as applied to a localized area of the body or to the surface of a body part, without necessarily involving target effect of the substance, making the classification rather a variant of the classification based on application location. In an enteral administration, the desired effect is systemic (non-local), substance is given via the digestive tract. In a parenteral administration, the desired effect is systemic, and substance is given by routes other than the digestive tract.

Non-limiting examples for topical administrations may include epicutaneous (application onto the skin), e.g., allergy testing or typical local anesthesia, inhalational, e.g. asthma medications, enema, e.g., contrast media for imaging of the bowel, eye drops (onto the conjunctiva), e.g., antibiotics for conjunctivitis, ear drops, such as antibiotics and corticosteroids for otitis externa, and those through mucous membranes in the body.

Enteral administration may be administration that involves any part of the gastrointestinal tract and has systemic effects. The examples may include those by mouth (orally), many drugs as tablets, capsules, or drops, those by gastric feeding tube, duodenal feeding tube, or gastrostomy, many drugs and enteral nutrition, and those rectally, various drugs in suppository.

Examples of parenteral administrations may include intravenous (into a vein), e.g. many drugs, total parenteral nutrition intra-arterial (into an artery), e.g., vasodilator drugs in the treatment of vasospasm and thrombolytic drugs for treatment of embolism, intraosseous infusion (into the bone marrow), intra-muscular, intracerebral (into the brain parenchyma), intracerebroventricular (into cerebral ventricular system), intrathecal (an injection into the spinal canal), and subcutaneous (under the skin). Among them, intraosseous infusion is, in effect, an indirect intravenous access because the bone marrow drains directly into the venous system. Intraosseous infusion may be occasionally used for drugs and fluids in emergency medicine and pediatrics when intravenous access is difficult.

As used herein, the term "intraperitoneal injection" or "IP injection" refers to the injection of a substance into the peritoneum (body cavity). IP injection is more often applied to animals than to humans. In general, IP injection may be preferred when large amounts of blood replacement fluids are needed, or when low blood pressure or other problems prevent the use of a suitable blood vessel for intravenous injection.

II. The Invention

In certain aspects, the disclosure is directed to the use of gadolinium-labeled alkylphosphocholine analogs for medical detection or detection/imaging of cancerous tumors or tumor cells in a subject or in a biological sample. In other aspects, the disclosure is directed to the use of gadolinium-labeled alkylphosphocholine analogs to treat cancer in a subject. In yet other aspects, the disclosure is directed to the gadolinium-labeled alkylphosphocholine analogs and methods of synthesizing such compounds.

A. Neutron Capture Therapy

Neutron capture therapy (NCT) is a non-invasive therapeutic method for treating locally invasive malignant tumors, such as primary brain tumors and recurrent head and neck cancer. In NCT, the patient is first injected with a tumor localizing drug containing a non-radioactive isotope that has a high propensity or cross section (a) to capture slow neutrons (the "capture agent"). The cross section of the capture agent is many times greater than that of the other elements present in tissues, such as hydrogen, oxygen, and nitrogen. In the second step, the patient is radiated with epithermal neutrons, which after losing energy as they penetrate tissue, are absorbed by the capture agent. The capture agent subsequently emits high-energy charged particles that can effectively kill cancerous tissue.

All of the clinical experience to date with NCT uses the non-radioactive isotope boron-10 as the capture agent. However, the Gd-labeled PLE analogs disclosed herein may be ideal neutron capture therapy agents, since these compounds exhibit malignant tumor selectivity, and $^{157}$Gd has the highest thermal neutron cross section of any stable nucleotide, namely 25900 barn, which 8 times that of Boron.

B. MRI Detection/Imaging

The disclosed compounds are the first long-lived tumor-specific MR contrast agent for general broad spectrum tumor imaging and characterization. In addition, the compounds the long-lived tumor-specific MR contrast agents disclosed herein are suitable for use in therapy response monitoring to both chemotherapy and radiotherapy, and are suitable tumor contrast agent for MRI guided external beam radiotherapy.

A course of cancer radiotherapy may extend over a time frame of 5 to 7 weeks. Therapy is delivered daily, making the administration of short-lived MR contrast agents impractical, due to their renal toxicity. Therefore, a long-lived tumor specific contrast agent that has a biological half-life of weeks rather than minutes to hours (e.g., the disclosed compounds) may be ideal for external beam radiotherapy.

The contrast agent would be administered a few days before the start of treatment simulation to allow for adequate accumulation of the agent in the tumor. Boost doses may have to be administered either weekly or biweekly during the course of therapy. An MRI simulation would be carried out and a treatment plan would be developed. The patient would then be treated using an MRI guided radiotherapy system, which are now becoming commercially available, and the long-lived tumor-targeted contrast agent would then be used to optimize the dose delivery and to track the tumor tracking during therapy delivery, since these MRI guided radiotherapy systems allow for fast intratreatment imaging.

Using such methods, a moving tumor can be tracked using such an agent over the course of therapy. However, as pointed out above, the utility of the disclosed long-lived tumor specific MRI contrast imaging agent goes far beyond radiotherapy. Such an imaging agent can also be employed for response monitoring of chemotherapy as well as radiotherapy. For this to be feasible one indeed needs long-lived tumor specific imaging agents that will be retained in tumor cells. As tumor cells die through apoptosis or undergo mitotic catastrophe, the imaging agent is released from the tumor cells, leading to changes in the resulting MRI signal that allow for assessment of therapy response.

C. Gadolinium-Labeled PLE Analogs

The disclosed structures utilize an alkylphosphocholine carrier backbone. Once synthesized, the agents must harbor formulation properties that render them suitable for injection while retaining tumor selectivity. A non-limiting exemplary series of Gd-PLE analogs follows (additional non-limiting examples were described previously). The structures shown include a chelating moiety to which the gadolinium ion is chelated to produce the final imaging or therapeutic agent.

1

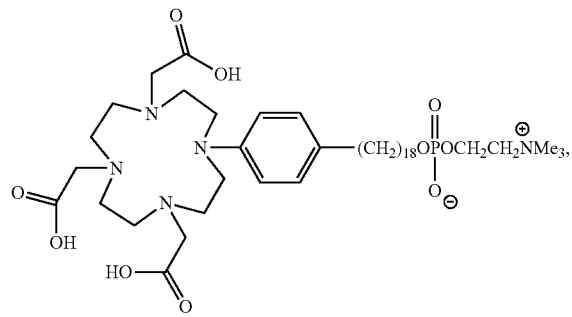

2

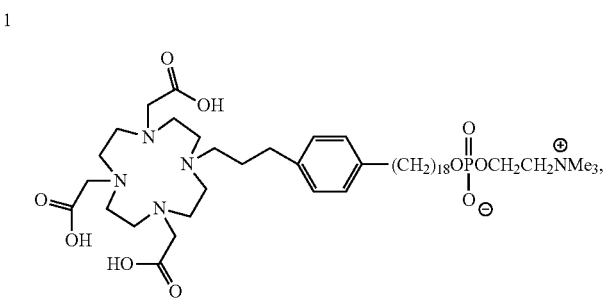

3

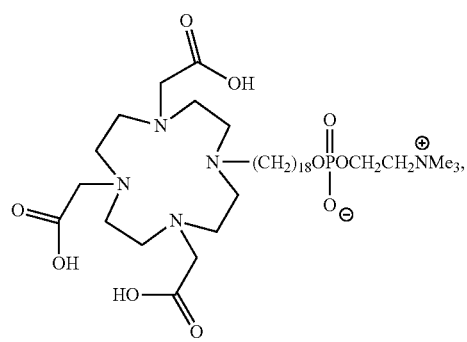

4

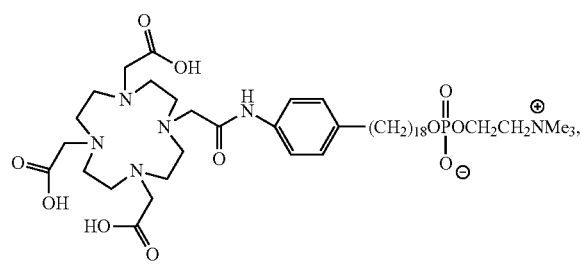

5

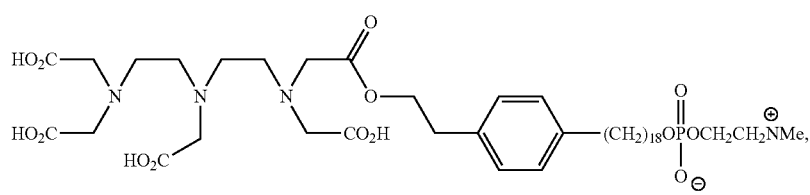

6

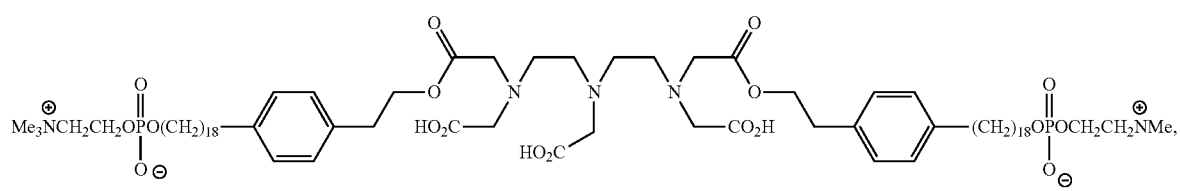

7

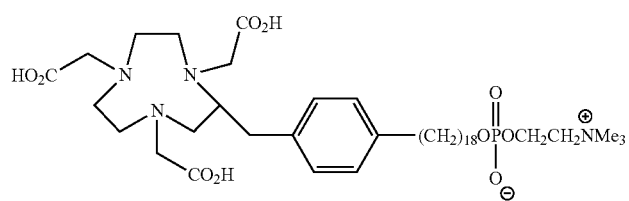

D. Methods of Synthesizing Exemplary Gd-PLE Analogs

Proposed synthesis of compound 1 is shown below. The first step of the synthesis is similar to described in *Org Synth*, 2008, 85, 10-14. The synthesis is started from cyclen which is converted into DO3A tris-Bn ester. This intermediate is then conjugated with NM404 in the presence of the base and Pd catalyst. Finally, benzyl protecting groups are removed by the catalytic hydrogenation.

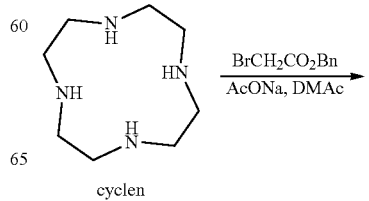

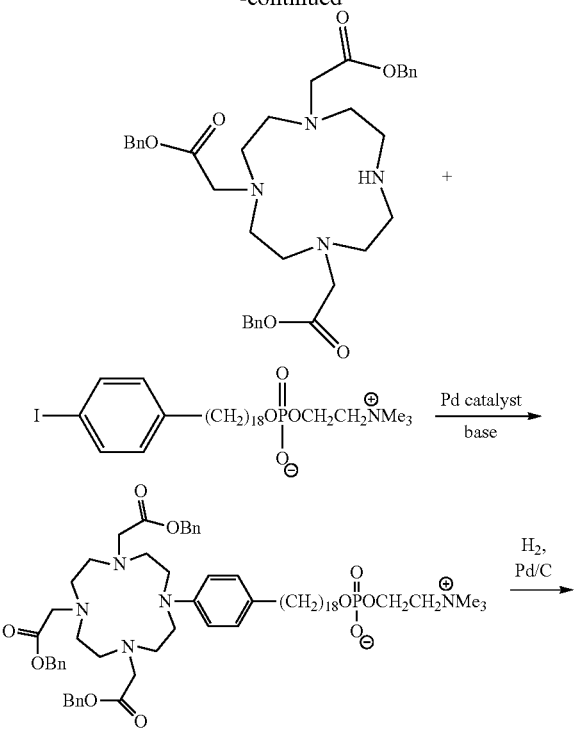

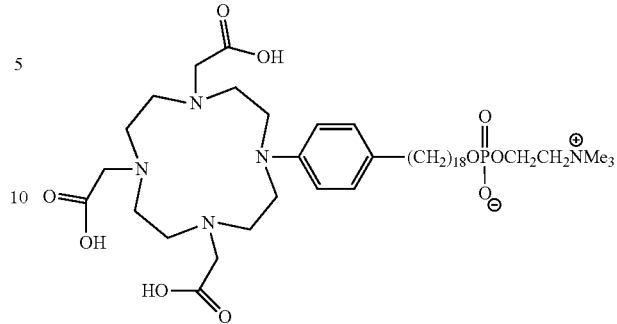

Synthesis of compound 2 is shown below. It begins with DO3A tris-Bn ester which is alkylated with 3-(bromo-prop-1-ynyl)-trimethylsilane. After alkylation, the trimethylsilyl group is removed and the intermediate acetylene is coupled with NM404 by the Sonogashira reaction. The benzyl groups are removed and the triple bond is hydrogenated simultaneously in the last step of the synthesis.

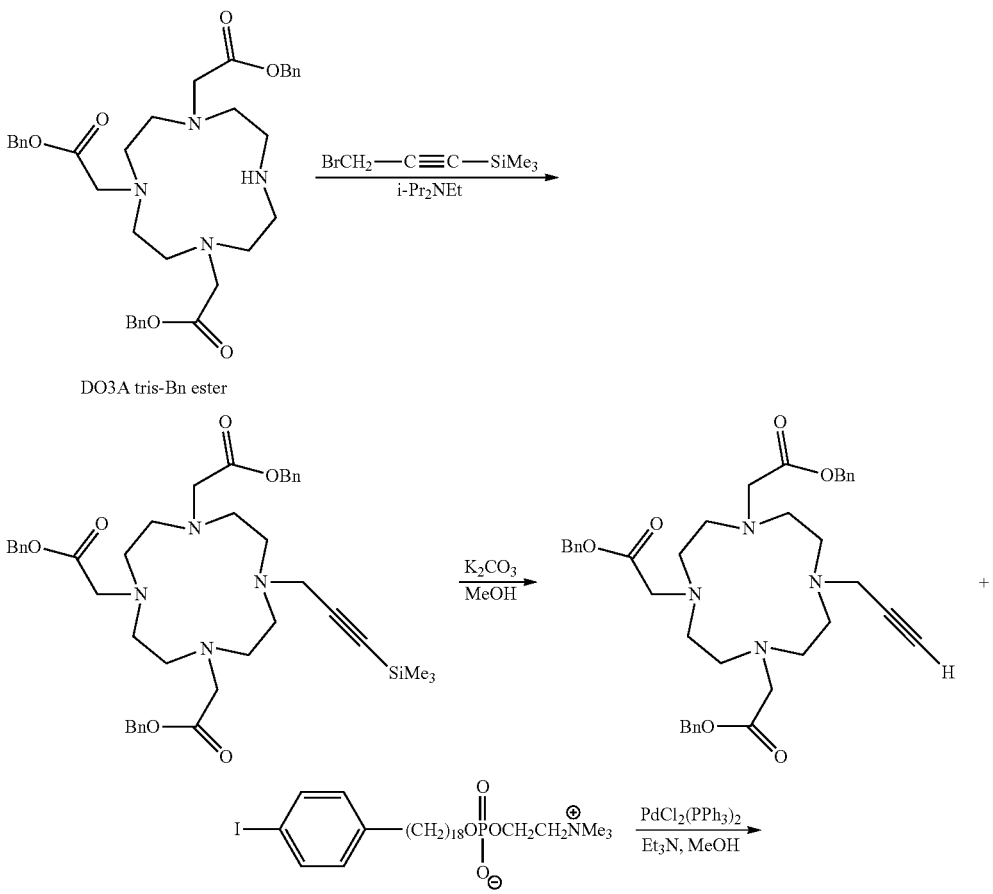

-continued
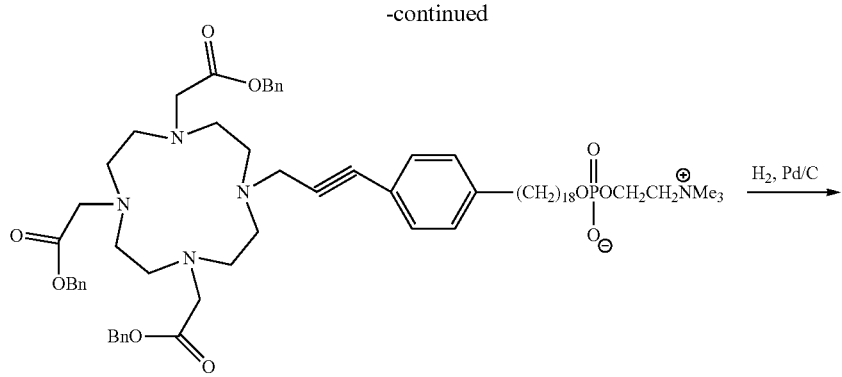
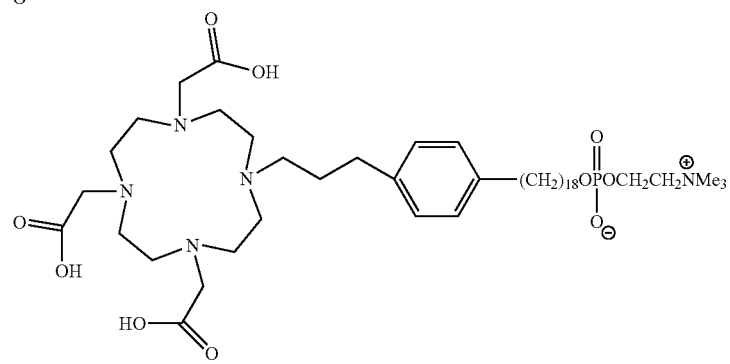
2
Compounds 5 and 6 can be synthesized from same precursors, DTPA dianhydride and 18-p-(3-hydroxyethyl-phenyl)-octadecyl phosphocholine as shown in the schemes below.
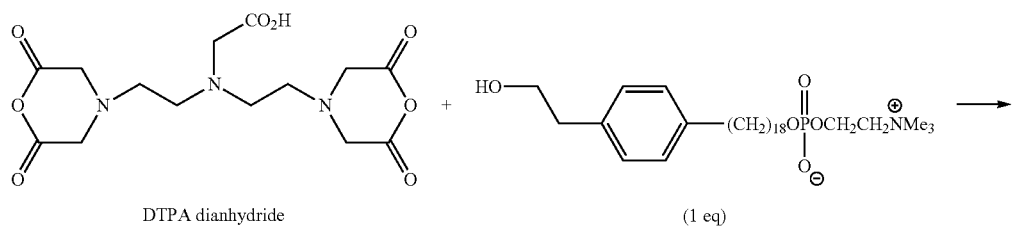
DTPA dianhydride  (1 eq)
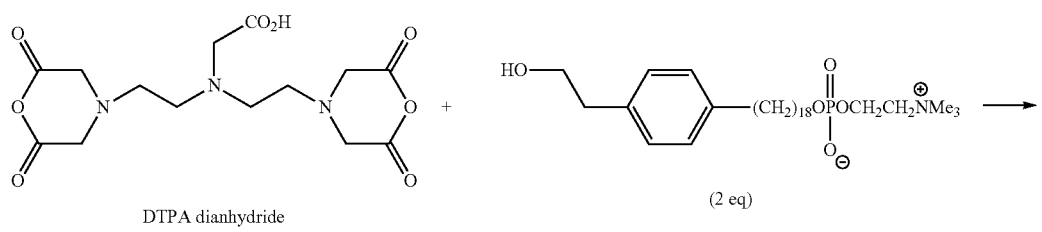
DTPA dianhydride  (2 eq)

-continued

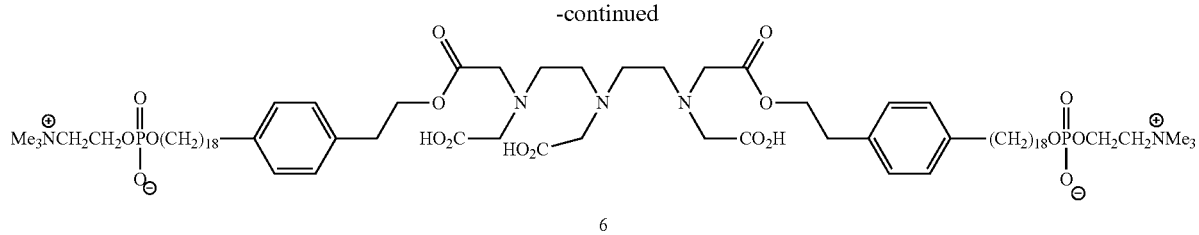

6

NOTA-NM404 conjugates can be synthesized in an analogous manner. One non-limiting example is NOTA-NM404 conjugate 7:

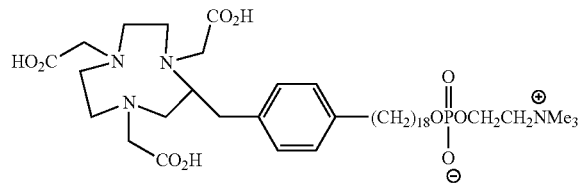

7

E. Dosage Forms and Administration Methods

Any route of administration may be suitable for administering the disclosed Gd-PLE analogs to a subject. In one embodiment, the disclosed analogs may be administered to the subject via intravenous injection. In another embodiment, the disclosed analogs may be administered to the subject via any other suitable systemic deliveries, such as oral, parenteral, intranasal, sublingual, rectal, or transdermal administrations.

In another embodiment, the disclosed analogs may be administered to the subject via nasal systems or mouth through, e.g., inhalation.

In another embodiment, the disclosed analogs may be administered to the subject via intraperitoneal injection or IP injection.

In certain embodiments, the disclosed analogs may be provided as pharmaceutically acceptable salts. Other salts may, however, be useful in the preparation of the analogs or of their pharmaceutically acceptable salts. Suitable pharmaceutically acceptable salts include, without limitation, acid addition salts which may, for example, be formed by mixing a solution of the analog with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid.

Where the disclosed analogs have at least one asymmetric center, they may accordingly exist as enantiomers. Where the disclosed alkylphosphocholine analogs possess two or more asymmetric centers, they may additionally exist as diastereoisomers. It is to be understood that all such isomers and mixtures thereof in any proportion are encompassed within the scope of the present disclosure.

The disclosure also includes methods of using pharmaceutical compositions comprising one or more of the disclosed analogs in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation.

For preparing solid compositions such as tablets, the principal active ingredient is mixed with a pharmaceutically acceptable carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture for a compound of the present invention, or a pharmaceutically acceptable salt thereof. The liquid forms in which the analogs may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium caboxymethylcellulose, methylcellulose, polyvinylpyrrolidone or gelatin.

The disclosed analogs are particularly useful when formulated in the form of a pharmaceutical injectable dosage, including in combination with an injectable carrier system. As used herein, injectable and infusion dosage forms (i.e., parenteral dosage forms) include, but are not limited to, liposomal injectables or a lipid bilayer vesicle having phospholipids that encapsulate an active drug substance. Injection includes a sterile preparation intended for parenteral use.

Five distinct classes of injections exist as defined by the USP: emulsions, lipids, powders, solutions and suspensions. Emulsion injection includes an emulsion comprising a sterile, pyrogen-free preparation intended to be administered parenterally. Lipid complex and powder for solution injection are sterile preparations intended for reconstitution to form a solution for parenteral use. Powder for suspension injection is a sterile preparation intended for reconstitution to form a suspension for parenteral use. Powder lyophilized for liposomal suspension injection is a sterile freeze dried preparation intended for reconstitution for parenteral use that is formulated in a manner allowing incorporation of liposomes, such as a lipid bilayer vesicle having phospholipids used to encapsulate an active drug substance within a lipid bilayer or in an aqueous space, whereby the formulation may be formed upon reconstitution. Powder lyophilized for solution injection is a dosage form intended for the solution prepared by lyophilization ("freeze drying"), whereby the process involves removing water from products in a frozen state at extremely low pressures, and whereby subsequent addition of liquid creates a solution that conforms in all respects to the requirements for injections. Powder lyophilized for suspension injection is a liquid preparation intended for parenteral use that contains solids suspended in a suitable fluid medium, and it conforms in all respects to the requirements for Sterile Suspensions, whereby the medicinal agents intended for the suspension are prepared by lyophilization. Solution injection involves a liquid preparation containing one or more drug substances dissolved in a suitable solvent or mixture of mutually miscible solvents that is suitable for injection.

Solution concentrate injection involves a sterile preparation for parenteral use that, upon addition of suitable solvents, yields a solution conforming in all respects to the requirements for injections. Suspension injection involves a liquid preparation (suitable for injection) containing solid particles dispersed throughout a liquid phase, whereby the particles are insoluble, and whereby an oil phase is dispersed throughout an aqueous phase or vice-versa. Suspension liposomal injection is a liquid preparation (suitable for injection) having an oil phase dispersed throughout an aqueous phase in such a manner that liposomes (a lipid bilayer vesicle usually containing phospholipids used to encapsulate an active drug substance either within a lipid bilayer or in an aqueous space) are formed. Suspension sonicated injection is a liquid preparation (suitable for injection) containing solid particles dispersed throughout a liquid phase, whereby the particles are insoluble. In addition, the product may be sonicated as a gas is bubbled through the suspension resulting in the formation of microspheres by the solid particles.

The parenteral carrier system includes one or more pharmaceutically suitable excipients, such as solvents and co-solvents, solubilizing agents, wetting agents, suspending agents, thickening agents, emulsifying agents, chelating agents, buffers, pH adjusters, antioxidants, reducing agents, antimicrobial preservatives, bulking agents, protectants, tonicity adjusters, and special additives.

The following examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

III. Examples

Summary:

In Example 1, we provide an exemplary synthesis that also finds use for the synthesis of analogous compounds chelating radioactive metal isotopes.

In Example 2, we demonstrate that an analog having a chelating agent and chelated metal substituted for the iodine moiety of NM404 (Gd-DO3A-404) is taken up by (and can be imaged in) solid tumor tissue, thus providing proof of concept for using the disclosed metal chelates as TRT and/or imaging agents.

In Example 3, we demonstrate the stability of Gd-DO3A-404.

In Example 4, we characterize the magnetic resonance (MR) relaxation characteristics ($r_1$ and $r_2$) of Gd-DO3A-404.

In Example 5, we extended the results of Example 2 to demonstrate the tumor-targeting capabilities and uptake dynamics of Gd-DO3A-404 in two different tumor models.

In Example 6, we report in-vivo biodistribution data for Gd-DO3A-404.

In Example 7, we demonstrate that the tumor-targeting properties of Gd-DO3A-404 reside in the NM404 targeting moiety. Specifically, we compare the tumor uptake and retention data for Gd-DO3A-404 with the same data obtained using DOTA-chelated $Gd^{3+}$ (DOTAREM®).

In Example 8, we demonstrate Gd-DO3A-404 uptake in an orthotopic glioblastoma model.

In Example 9, we disclose biodistribution data for Gd-DOA-404 after being administered to flank A549 xenograft mice.

In Example 10, we demonstrate Gd-DO3A-404 uptake in a triple-negative breast cancer model.

In Example 11, we demonstrate Gd-DO3A-404 uptake in two orthotopic xenograft models.

In Example 12, we demonstrate simultaneous uptake and imaging (PET and MRI) of the gadolinium chelate Gd-DO3A-404, acting as an MRI contrast agent, and the copper radionuclide Cu-64 chelate $^{64}$Cu-DO3A-404, which acts as a PET contrast agent.

Example 1: Synthesis of Metal Chelated DO3A-404

In this Example, we show the synthetic scheme used to synthesize one exemplary phospholipid chelate, Gd-DO3A-404.

Scheme for synthesizing Gd-DO3A-404:

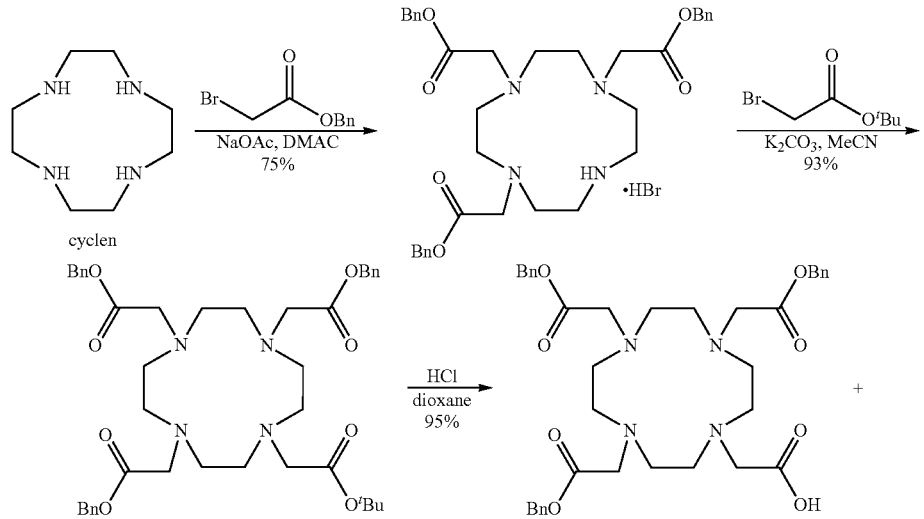

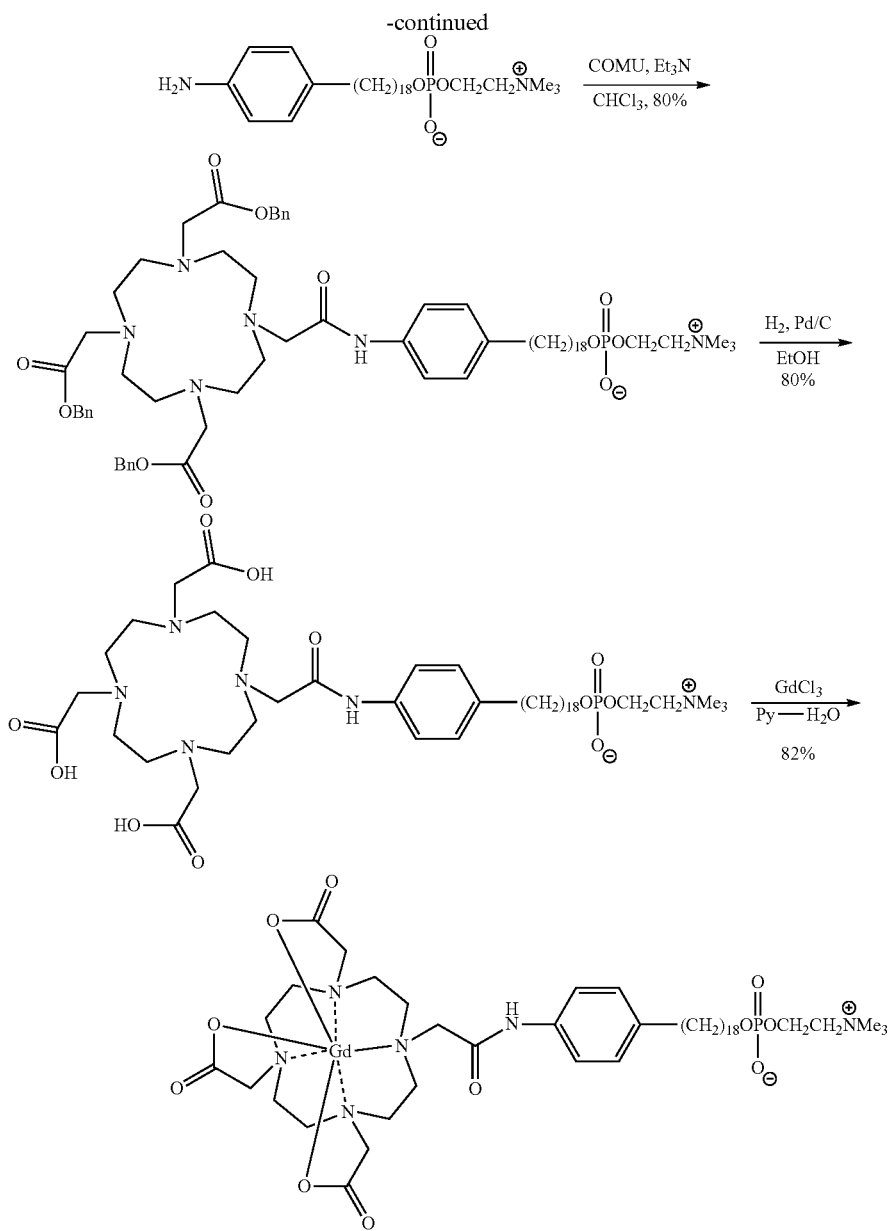

Example 2: In Vivo Imaging Proof of Concept

In this example, we demonstrate the successful in vivo MRI imaging of a tumor, using Gd-DO3A-404 as the MRI contrast agent.

For proof-of-concept in vivo imaging of tumor uptake of the Gd-DO3A-404 agent, nude athymic mouse with a flank A549 tumor (non small cell lung cancer) xenograft was scanned. The Gd-DO3A-404 agent (2.7 mg) was delivered via tail vein injection. Mice were anesthetized and scanning performed prior to contrast administration and at 1, 4, 24, 48, and 72 hours following contrast delivery. Imaging was performed on a 4.7 T Varian preclinical MRI scanner with a volume quadrature coil. T1-weighted images were acquired at all imaging time points using a fast spin echo scan with the following pulse sequence parameters: repetition time (TR)=206 ms, echo spacing=9 ms, echo train length=2, effective echo time (TE)=9 ms, 10 averages, with a 40×40 mm$^2$ field of view, 192×192 matrix, 10 slices of thickness 1 mm each.

Figure 2:
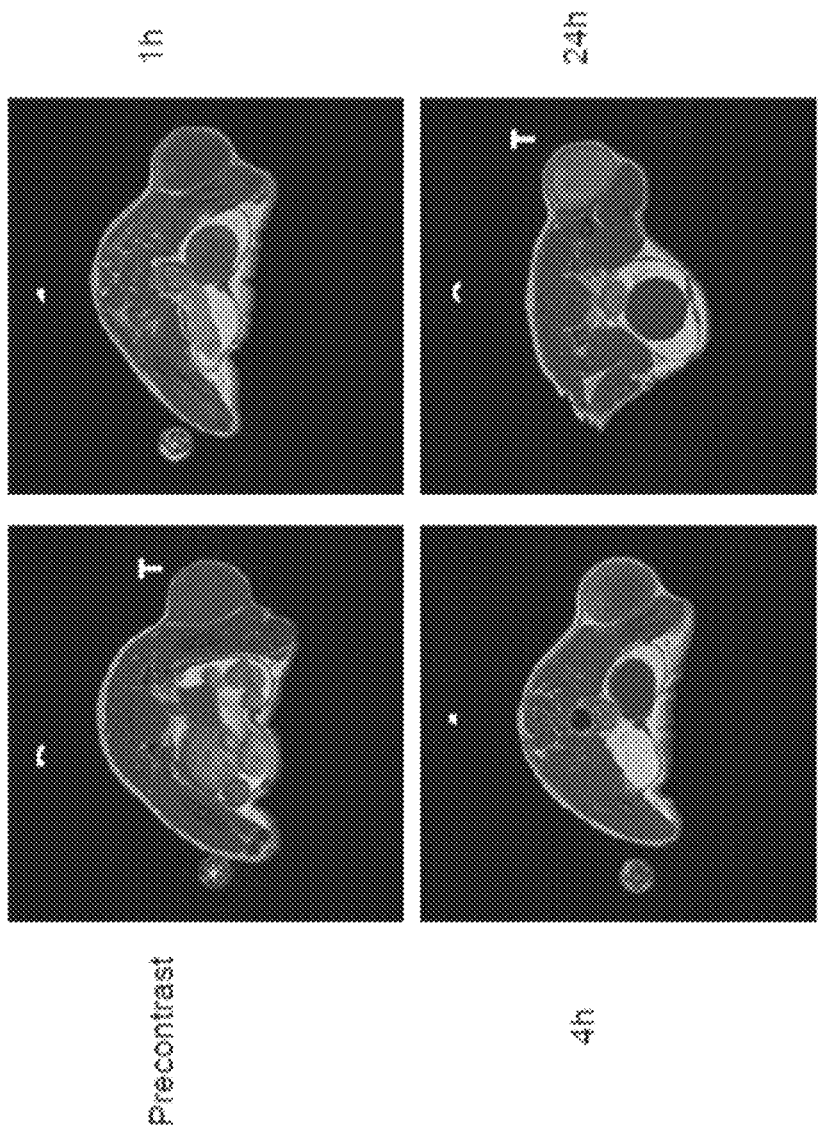
FIG. 2 shows a time course MRI image of a tumor-bearing mouse following injection of Gd-DO3A-404 showing enhancement of the tumor (T) by 24 hours.

As seen in FIG. 2, MRI imaging of the tumor was significantly enhanced by 24 hours post-injection.

These results demonstrate that the differential uptake and retention of alkylphosphocholine analogs is maintained for the gadolinium chelated analogs disclosed herein. Thus, the disclosed gadolinium chelates can readily be applied to clinical therapeutic and imaging applications.

Example 3: Stability of Gd-DO3A-404

In this example, we quantitated the free Gd concentration associated with Gd-DO3A-404. The results demonstrate that Gd-DO3A-404 is quite stable, and substantially retains the chelated Gd (III) ion. Thus, it is suitable for use as a tumor-targeting agent for use in imaging and/or therapeutic applications.

We considered several methods that are conventionally employed to quantitate the free Gd (III) ion concentration. First, we considered using chromophoric ligands. For example, using Xylenol Orange, free Gd(III) can be reliably detected down to concentrations of 1 μM. This detection limit is too high to reliably detect free Gd in this context. The 5-Br-PADAP ligand provides a significantly lower detection limit, down to 0.1 μM Gd(III). However, we observed a detrimental interaction between the ligand the Gd-DO3A-404 that rendered this method unusable in this context.

Next, we considered using membrane-based separation approaches. However, such methods proved to be problematic in this context, due to retainment of the free Gd by the membrane.

After considering other alternatives, we decided to determine free Gd concentration by selective chelation and separation of the free Gd. We separated the Gd-DO3A-404 complex from free Gd (III) ion by CHELEX® solid phase extraction (as described by Raju, et al., J. Anal. At. Spectrom. 25 (2010), 1573-1580). Specifically, using a CHELEX® solid phase extraction column comprising an immobilized ligand (iminodiacetate) with very high affinity for free ion species of multi-valent transition and rare-earth metals, Gd was retained and then eluted using a known ratio of chelated Gd-DO3A-404 and acid-digested Gd-DO3A-404. The sample was the analyzed by magnetic sector ICP-MS to determine the concentration of free Gd. The free Gd concentration was found to be 0.081%.

Example 4: Gd-DO3A-404 Shows Favorable Relaxivity for $T_1$-Weighted Imaging

In this example, we characterized the magnetic resonance relaxation characteristics of Gd-DO3A-404, which compare favorably to the characteristics of commonly used contrast agents.

For initial studies, relaxivity was measured at 4.7 T. Longitudinal relaxivity, which is defined by the linear relationship between $R_1$ relaxation rate and concentration, was measured using an inversion recovery spin echo sequence.

Figure 3:
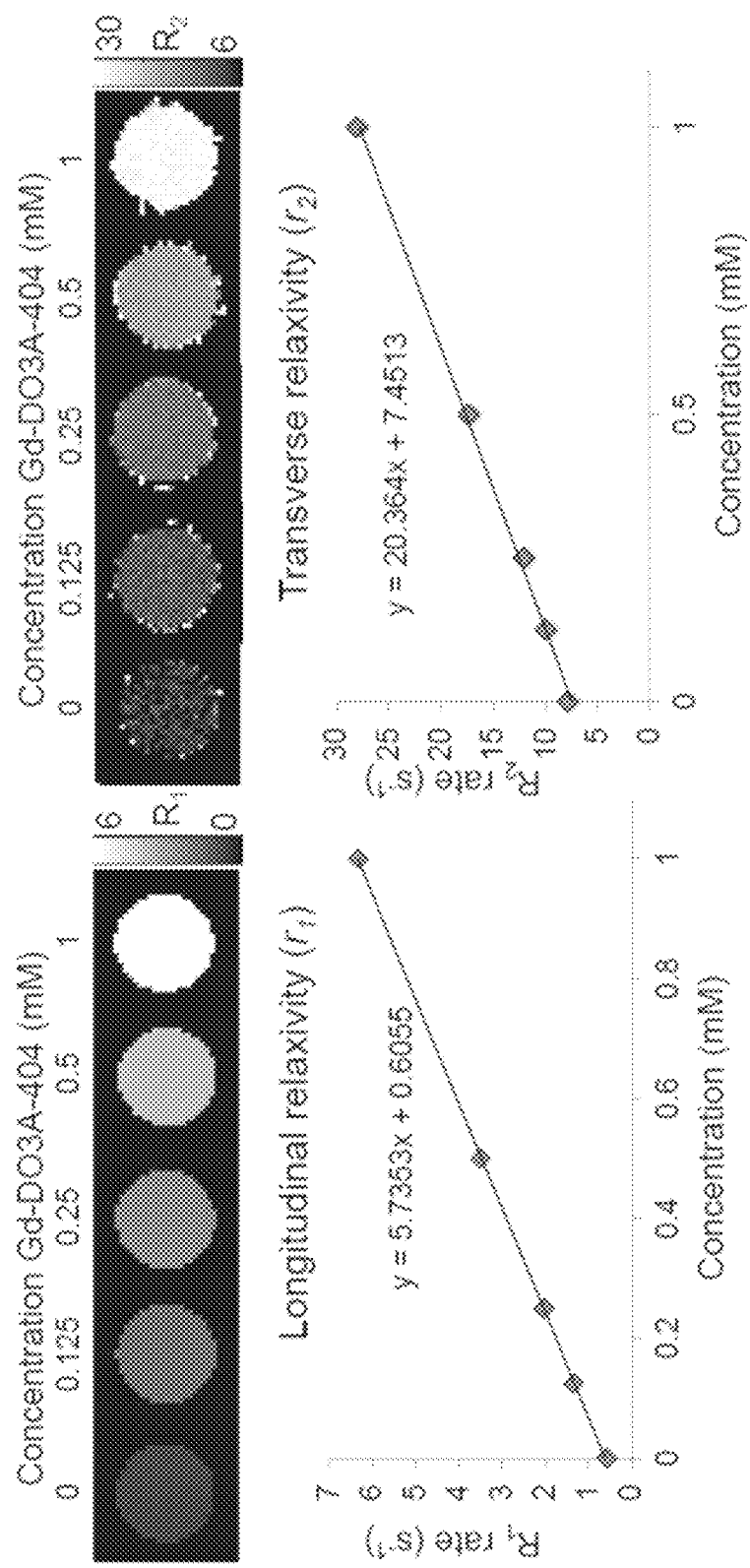
FIG. 3 (left panel) shows $R_1$ relaxation rate as a function of Gd-DO3A-404 concentration, both as $T_1$-weighted images (top left) and plotted as a graph (bottom left). The linear relationship shown by the graph defines longitudinal relaxivity ($r_1$).

Higher relaxivity results in brighter signal on a $T_1$-weighted image, and thus indicates greater $T_1$-weighted signal enhancement potential. By plotting $R_1$ (=1/T1) versus concentration at five different concentrations of the Gd-DOTA-404 agent and determining the equation of the resulting line (see FIG. 3, left panel), we calculated a longitudinal relaxivity in plasma of 5.74 s-1/mM. This compares favorably to clinical $T_1$ shortening contrast agents (such as DOTAREM®), which have been shown to have relaxivities of 2-3 s-1/mM at this field strength.

Similarly, by plotting $R_2$ versus concentration at five different concentrations of the Gd-DOTA-404 agent and determining the equation of the resulting line (see FIG. 3, right panel), we calculated a transverse relaxivity in plasma of 20.4 s-1/mM. Thus, $r_2$ relaxivity is also favorably increased when using Gd-DOTA-404 as a contrast agent (see FIG. 3, right panel).

Determination of $r_1$ of the agent in saline, excipient, and plasma showed that it consistently resulted in shortened $T_1$ times. See Table 1.

TABLE 1

Longitudinal Relaxivity ($r_1$) and Transverse Relaxivity ($r_2$) of Gd-DO3A-404

| | Relaxivity of Gd-DO3A-404 ($s^{-1}$/mM) | | |
|---|---|---|---|
| | In saline | In excipient | In plasma |
| $r_1$ | 5.68 | 5.84 | 5.74 |
| $r_2$ | 16.14 | 11.31 | 20.36 |

These data demonstrate that the disclosed gadolinium chelated analogs would be effective contrast agents for magnetic resonance imaging applications.

Example 5: In Vivo Cancer Imaging in Multiple Tumor Models

In this extension of Example 2, we demonstrate selective uptake and in vivo MRI imaging in two distinct flank tumor types, using Gd-DO3A-404 as the MRI contrast agent.

To test uptake and retention in rodent models of human cancer, flank xenografts were established in mice for two distinct tumor types, A549 (human non small cell lung cancer, NSCLC) and U87 (human glioma). N=3 for each model. For pre-contrast imaging, $T_1$-W images of the tumor and abdomen (FIG. 4; 2 leftmost images) and $T_1$ maps of the tumor were obtained.

At time zero ("contrast"), 2.5 mg of Gd-DO3A-404 (~12 mmol/kg body mass) was delivered into the mice by intravenous injection. Animals were scanned pre-contrast and at various time points between one hour and seven days post-contrast (after one hour, 24 hours, 48 hours, three days, four days and seven days). $T_1$ maps of the tumor were acquired for each time point, along with $T_1$-weighted images of the tumor and the abdomen (see FIGS. 4 and 5).

Figure 4:
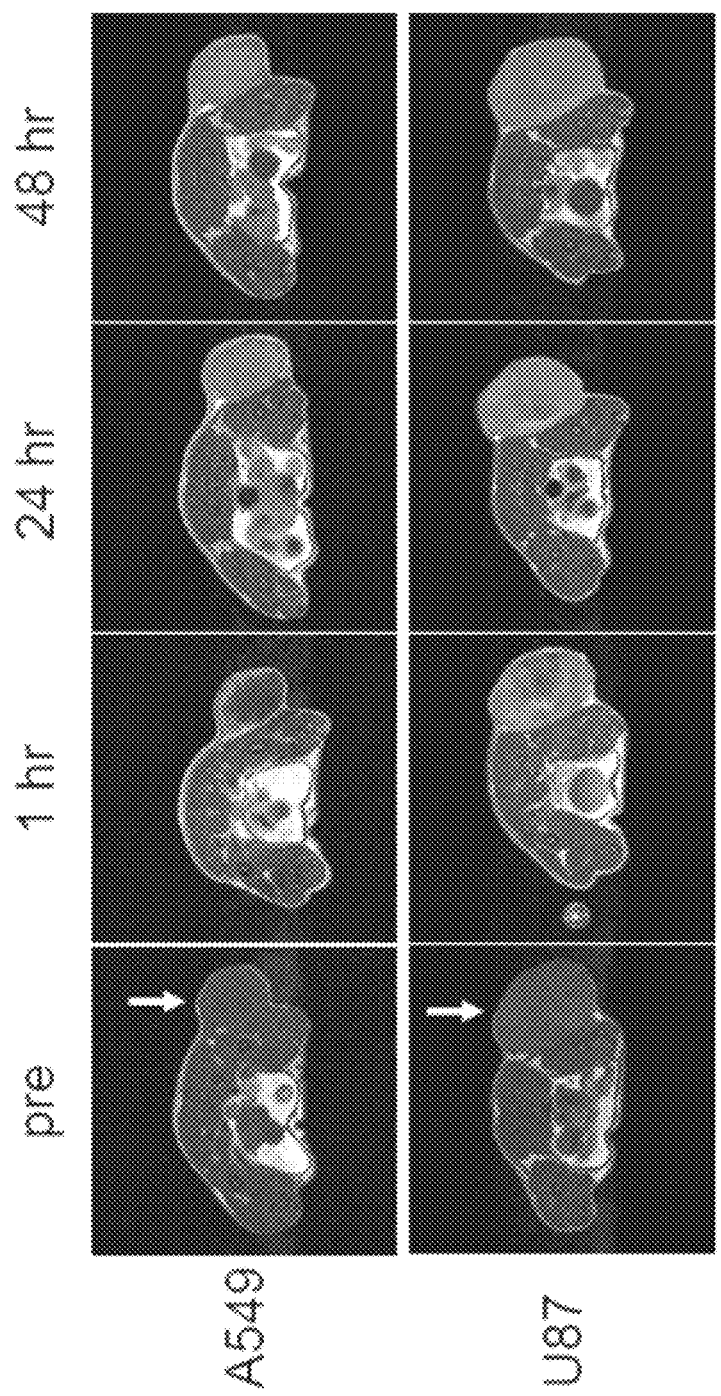
FIG. 4 shows time course MRI images of tumor-bearing mice. The top panel includes images of a mouse bearing a flank A549 (human NSCLC) tumor before contrast agent injection (left, arrow showing tumor location), one hour after injection of Gd-DO3A-404 (second from left), 24 hours following injection of Gd-DO3A-404 (third from left), and 48 hours following injection of Gd-DO3A-404 (rightmost image). The bottom panel includes images of a mouse bearing a flank U87 (human glioma) tumor before contrast agent injection (leftmost image, arrow showing tumor location), one hour after injection of Gd-DO3A-404 (second from left), 24 hours following injection of Gd-DO3A-404 (third from left), and 48 hours following injection of Gd-DO3A-404 (rightmost image).
Figure 5:
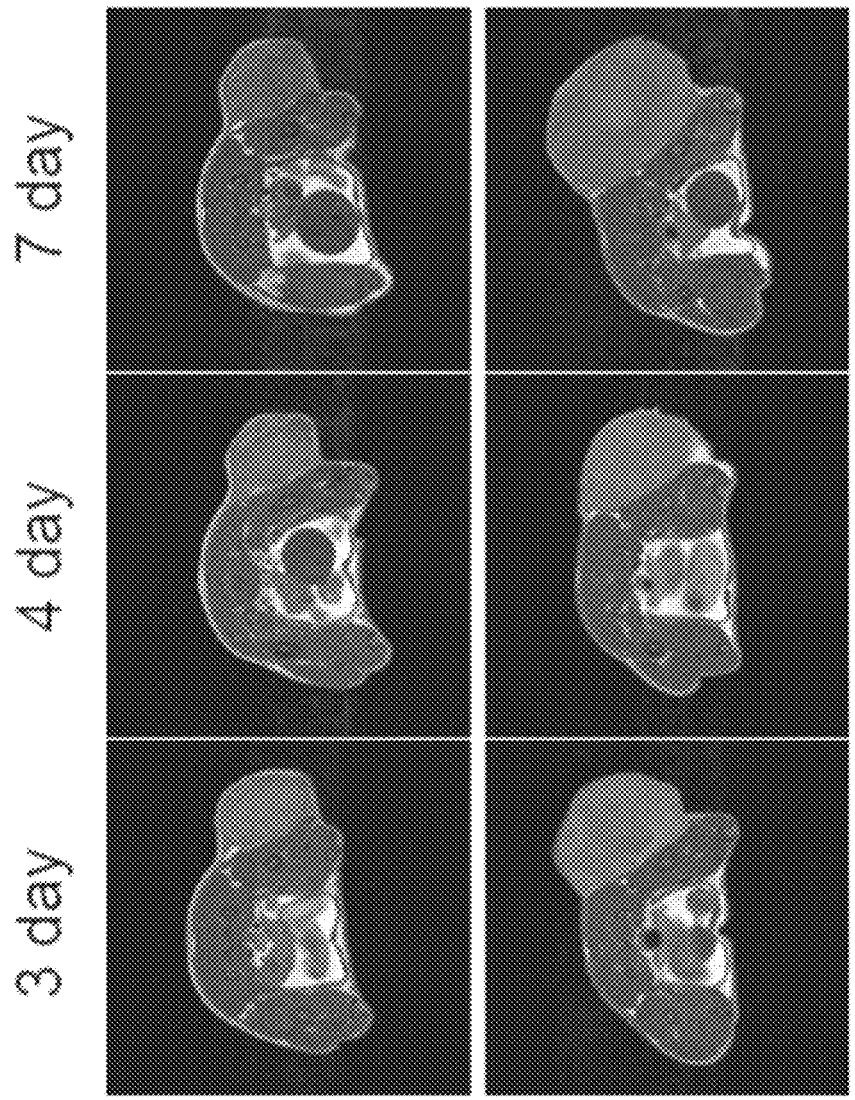
FIG. 5 shows further time course MRI images of tumor-bearing mice, continuing from FIG. 4. The top panel includes images of the mouse bearing a flank A549 (human NSCLC) tumor three days after injection of Gd-DO3A-404 (leftmost image), four days following injection of Gd-DO3A-404 (second from left), and seven days following injection of Gd-DO3A-404 (rightmost image). The bottom panel includes images of the mouse bearing a flank U87 (human glioma) tumor three days after injection of Gd-DO3A-404 (leftmost image), four days following injection of Gd-DO3A-404 (second from left), and seven days following injection of Gd-DO3A-404 (rightmost image).

In the NSCLC model, Gd-DO3A-404 uptake was not immediate and reached a maximum at 24-48 hours post-contrast (FIG. 4). The uptake was maintained over several days (FIG. 5). In the U87 model, uptake was more rapid (already observable at one hour after delivery; see FIG. 4) and appeared to reach higher levels and was maintained for a longer time period (see FIG. 5).

Figure 6:
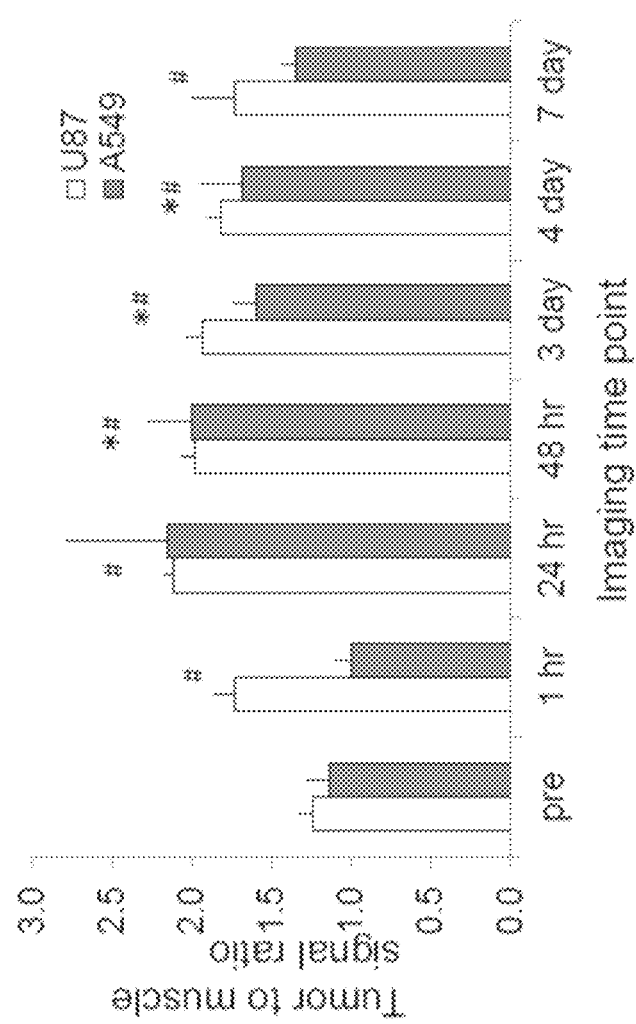
FIG. 6 is a bar graph of quantified results from the images shown in FIGS. 4 and 5. Specifically, the tumor to muscle T1-weighted signal ratios are shown for both the mouse bearing a flank A549 (human NSCLC) tumor (shaded bar) and the mouse bearing a flank U87 (human glioma) tumor (unshaded bar) before contrast agent injection (pre), one hour after injection of Gd-DO3A-404, 24 hours after injection of Gd-DO3A-404, 48 hours after injection of Gd-DO3A-404, three days after injection of Gd-DO3A-404, four days after injection of Gd-DO3A-404, and seven days after injection of Gd-DO3A-404. *$p<0.05$ compared to pre-contrast, A549. #$p<0.05$ compared to pre-contrast, U87.
Figure 7:
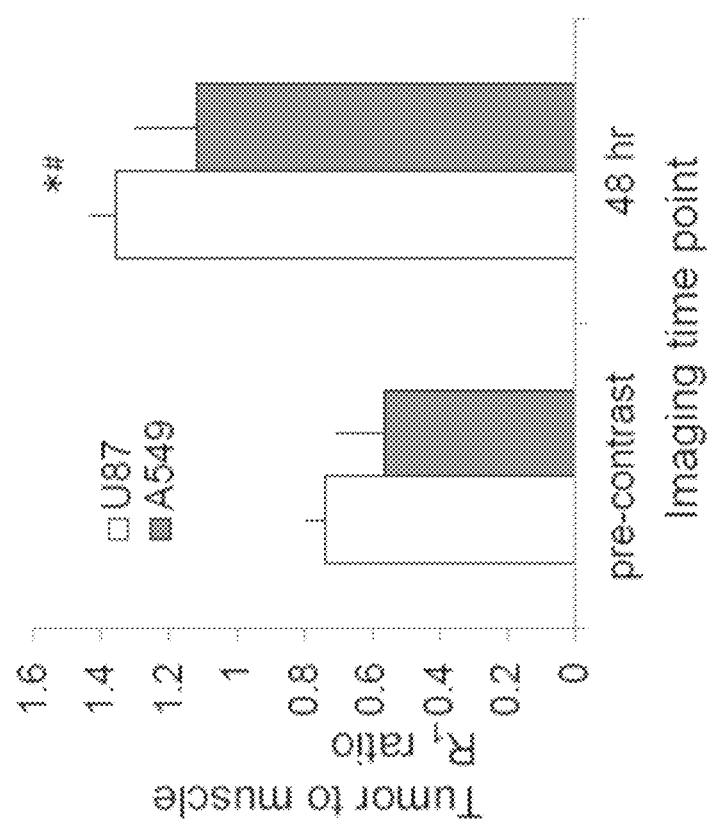
FIG. 7 is a bar graph of quantified results from the images shown in FIGS. 4 and 5. Specifically, the tumor to muscle $R_1$ ratios are shown for both the mouse bearing a flank A549 (human NSCLC) tumor (shaded bar) and the mouse bearing a flank U87 (human glioma) tumor (unshaded bar) before contrast agent injection (pre-contrast), and 48 hours after injection of Gd-DO3A-404. *$p<0.05$ compared to pre-contrast, A549. #$p<0.05$ compared to pre-contrast, U87.
Figure 8:
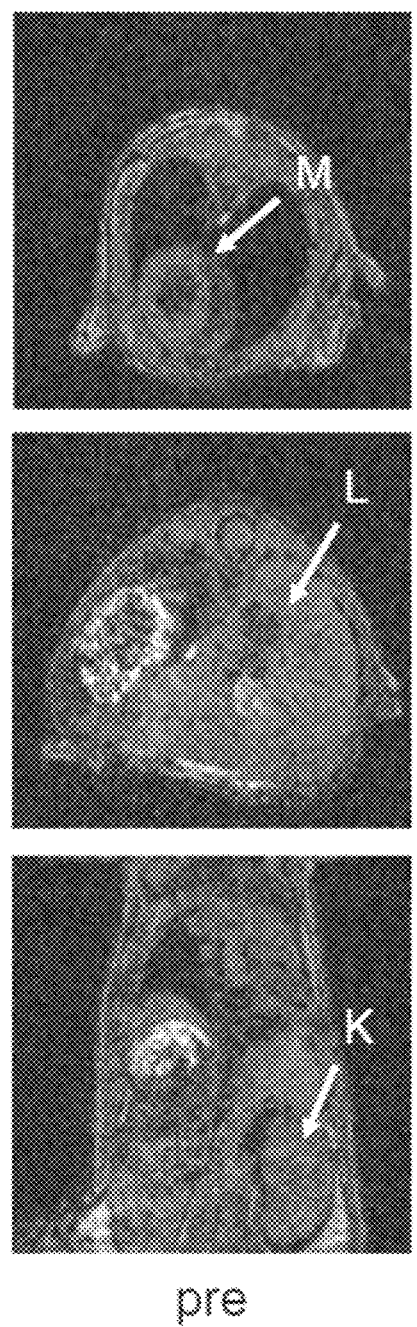
FIGS. 8, 9, 10, 11 and 12 are T1-weighted spoiled gradient (SPGR) magnetic resonance (MR) images of three different mouse abdomen cross-sections, showing in vivo biodistribution of the Gd-DO3A-404 contrast agent.
Figure 9:
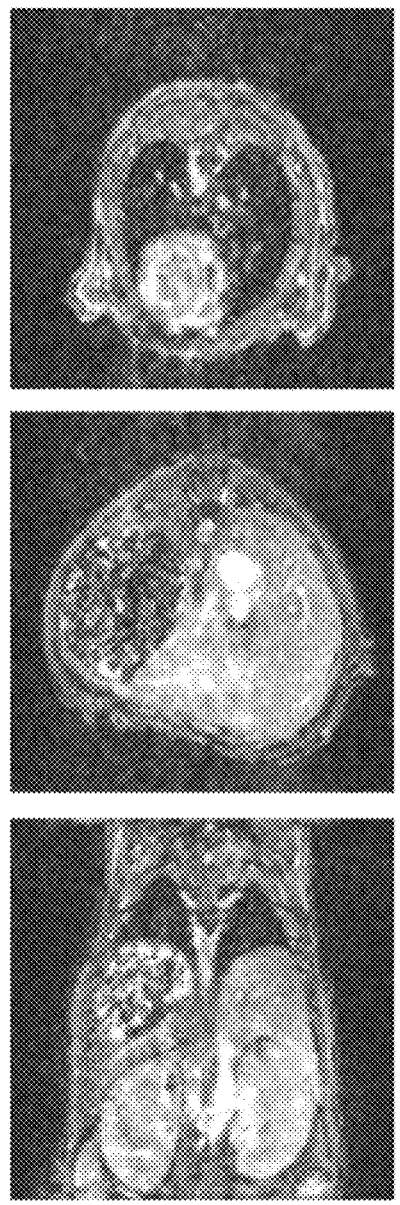
Figure 10:
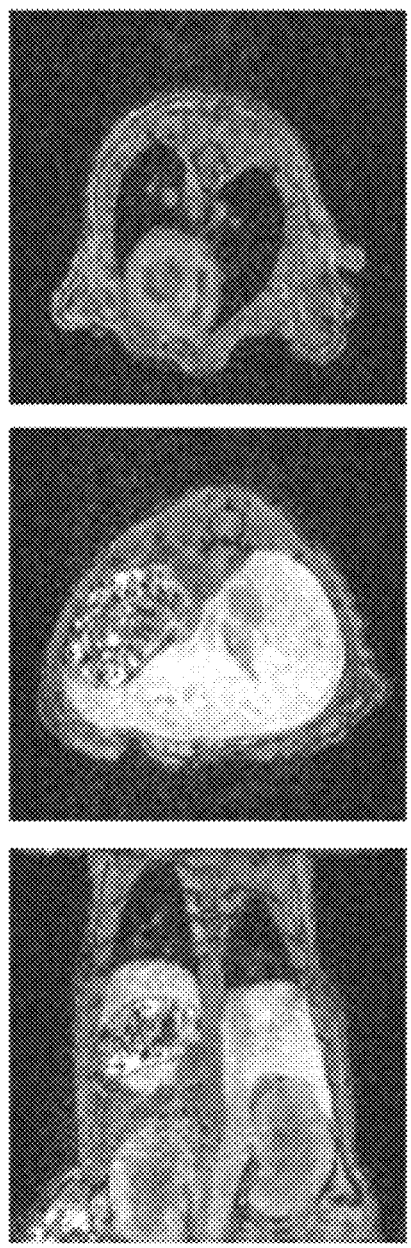
Figure 11:
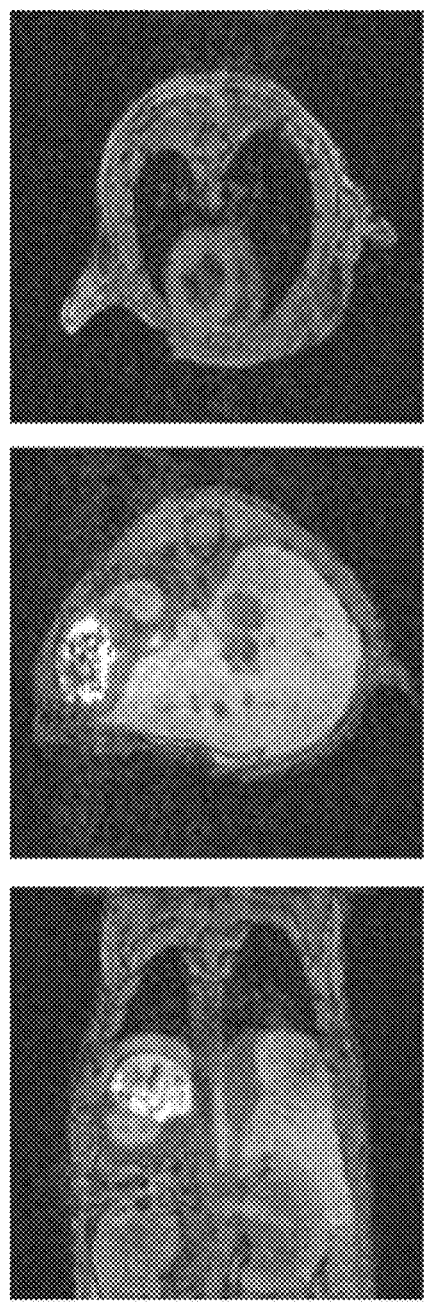

Those observations were confirmed by the quantified data, where tumor to muscle T1-weighted signal ratios were approximately doubled following Gd-DO3A-404 delivery (FIG. 6). The increase in tumor signal was more rapid and more prolonged in U87 tumors as compared to A549 tumors. As seen in FIG. 7, the $R_1$ relaxation rate for both tumor types was significantly increased at 48 hours post-contrast.

These results demonstrate that the differential uptake and retention of alkylphosphocholine analogs in multiple tumor types is maintained for the gadolinium chelated analogs disclosed herein. Thus, the disclosed gadolinium chelates can readily be applied to clinical therapeutic and imaging applications.

Example 6: Use of MRI to Determine In Vivo Biodistribution of Gd-DO3A-404

In this example, we determined the in vivo biodistribution of the Gd-DO3A-404 after the contrast agent was administered (see Example 5). During the course of performing the experiments described in Example 4, we also acquired $T_1$-weighted spoiled gradient (SPGR) images in the abdomen of the mice, to observe biodistribution. Abdominal cross-sections imaged included the myocardium (FIGS.

Figure 12:
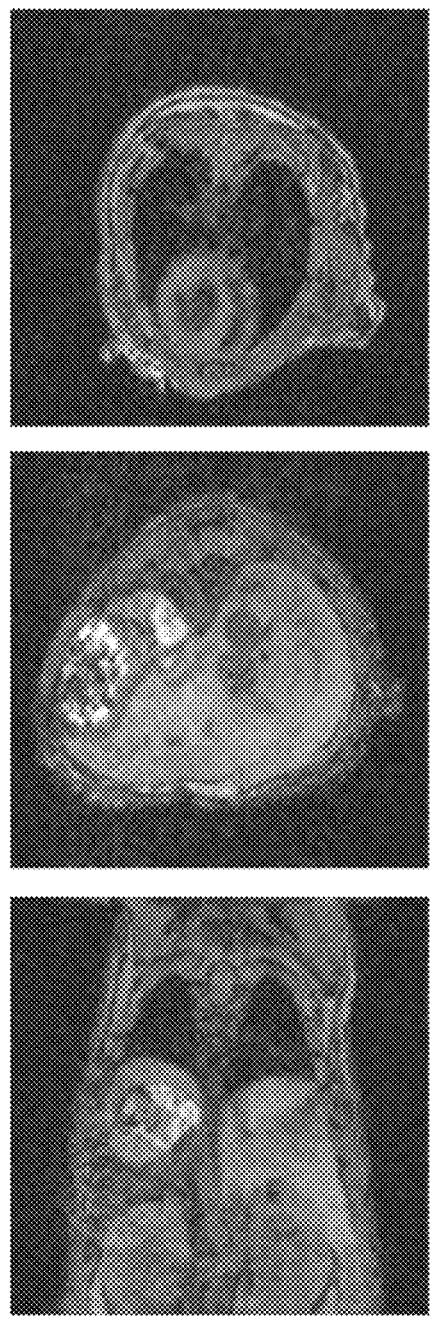

8-12, top image), the liver (FIGS. 8-12, center image), and a kidney (FIGS. 8-12, bottom image). Images are shown pre-contrast (FIG. 8), and at one hour (FIG. 9), 24 hours (FIG. 10), four days (FIG. 11) and seven days post-contrast (FIG. 12).

In the myocardium and blood pool, the Gd-DO3A-404 contrast agent circulates for nearly up to a day, after which any signal observed is due to retention rather than from further uptake. In the liver and kidney, the Gd-DO3A-404 contrast agent is substantially cleared over time, with more rapid clearance occurring through the liver, and more prolonged clearance occurring through the kidney. Notably, the Gd-DO3A-404 contrast agent exhibits a P-kinetic profile, including hepatobiliary excretion, that is similar to that of related alkylphosphocholine analogs.

Example 7

The Gd-DO3A-404 Targeting Moiety Facilitates Tumor-Selective and Sustained Uptake In this example, we demonstrate that the selective uptake and retention of Gd-DO3A-404 in tumor tissues is in fact facilitated by the tumor-targeting phospholipid moiety (the "404" moiety; see FIG. 1), rather than by the gadolinium metal or its chelating agent. Accordingly, this Example demonstrates that effective tumor-targeting contrast agents are not limited to those having a specific chelating agent, as long as they include the disclosed tumor-targeting phospholipid moieties.

Figure 13:
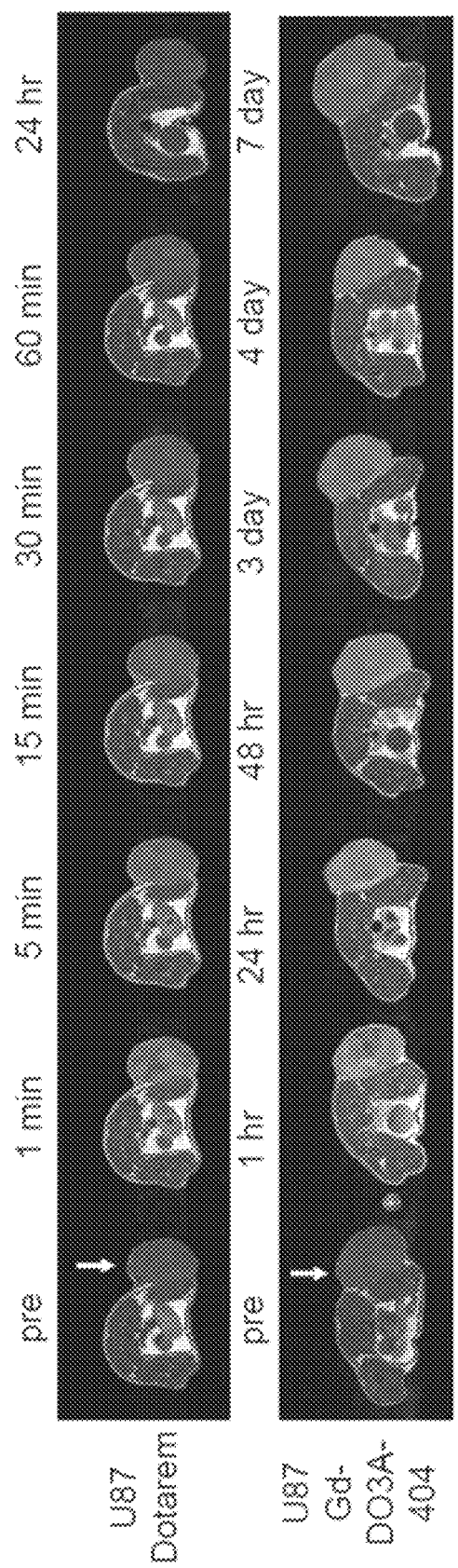
FIG. 13 shows a time course MRI image of tumor-bearing (U87) mice before (pre) and for various times following injection of DOTA-chelated $Gd^{3+}$ (DOTAREM®, top panel) and Gd-DO3A-404 (bottom panel). Tumor location in the mouse flank is indicated by the arrow in the two "pre" images.

To verify that uptake and retention was due to targeting of the "404" moiety, we directly compared the uptake of Gd-DO3A-404 with that of DOTA-chelated $Gd^{3+}$ (DOTA-REM®) in an identical tumor model (mice with flank U87 tumors) and imaging scenario, using the same number of moles of each. As seen in FIG. 13, the uptake and clearance of DOTAREM®, is much more rapid than that of Gd-DO3A-404.

Figure 14:
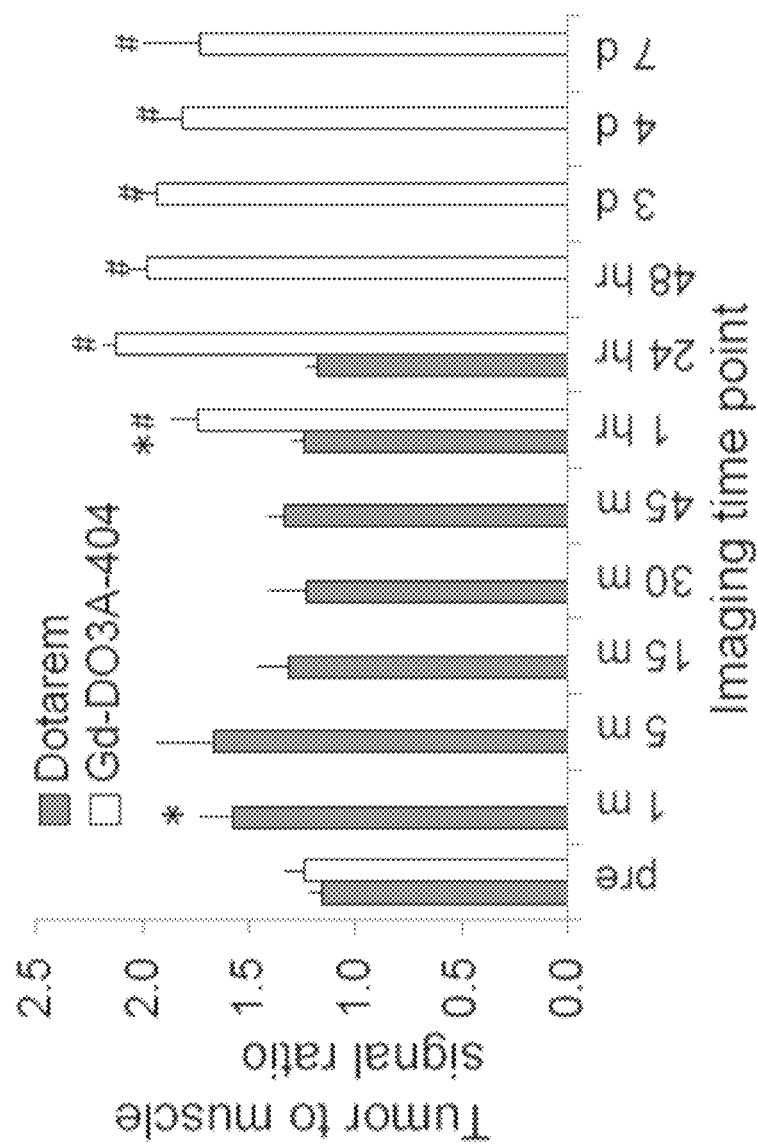
FIG. 14 is a bar graph is a bar graph of quantified results from the images shown in FIG. 13. Specifically, the tumor to muscle signal ratios are shown for both the U87 mouse before (pre) and at various times after injection with DOTAREM® (shaded bars) or Gd-DO3A-404 (unshaded bars). *$p<0.05$ compared to pre-contrast, DOTAREM®. #$p<0.05$ compared to pre-contrast, Gd-DO3A-404.

We the quantified the tumor to muscle ratio and compare it to baseline scans. As seen in FIG. 14, the DOTOREM® uptake was less striking, and significant only at a couple of early time points, as compared to Gd-DO3A-404.

These results show that the phospholipid targeting moiety of Gd-DO3A-404 (the 404 moiety), not the chelating agent and chelated metal (the Gd-DO3A moiety) are responsible for the observed selective tumor uptake and retention. Thus, a variety of different chelating moieties can be used without affecting the selective tumor uptake and retention properties of the disclosed chelates.

Example 8: Brain Tumor Uptake of Gd-DO3A-404 in Orthotopic Glioma Model

In this example, we demonstrate that at higher dosages, Gd-DO3A-404 can pass through the blood-brain barrier to successfully target brain tumor tissue.

To investigate the use of Gd-DO3A-404 to detect tumors and metasteses in situ, in particular, in the brain, we created an orthotopic glioblastoma model using cancer stem cells injected into the brain. To create the model, brains of mice were injected with cells from orthotopic glioblastoma stem cell line 12.6. After sufficient tumor growth, monitored with T2-weighted MRI, we imaged subjects pre-contrast and after delivery (24-72 hours) of two different doses of Gd-DO3A-404 (2.5 or 3.7 mg; ~0.12-0.18 mmole/kg).

Figure 15:
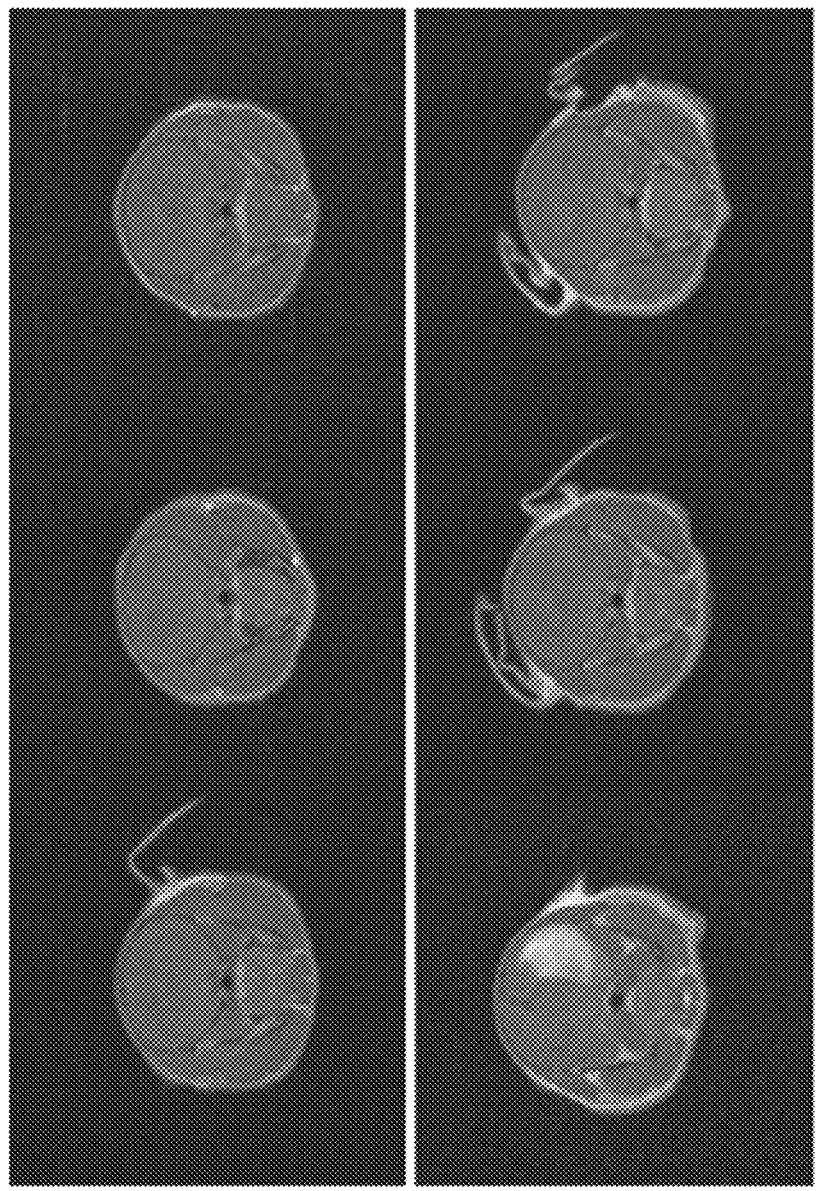
FIG. 15 shows MRI brain images of orthotopic glioblastoma model mice. 2.5 mg (top panel) or 3.7 mg (bottom panel) of Gd-DOA3A-404 was administered to the mice by intravenous injection, and these images were obtained 48 hours after contrast agent injection.

At the lower dose used for flank xenografts, no brain uptake was observed (see FIG. 15, upper panel). Because the lower delivered dose was relatively low (on the same order of that delivered per kg body weight in clinical settings), we increased the dose for another group of animals. In this group, we observed uptake in one subject (FIG. 15, bottom panel). This result indicates that the blood-brain barrier (BBB) may be playing a role in brain tumor uptake, and dosage may be "tuned" to facilitate the contrast agent's passage through the BBB.

Example 9: In Vivo Biodistribution Data for Gd-DO3A-404 in Flank A549 Xenograft Mice In this extension of Example 6, we further examined the in vivo biodistribution of Gd-DO3A-404 after it is administered. Specifically, tissue biodistribution was measured in A549-flank bearing mice 72 hours after administration of Gd-DO3A-404. Nude athymic mice were sacrificed, perfused and tissues were collected and quantitated for Gd by high-resolution (magnetic-sector) inductively-coupled plasma mass spectrometry (SF-ICPMS). n=3 mice.

Figure 16:
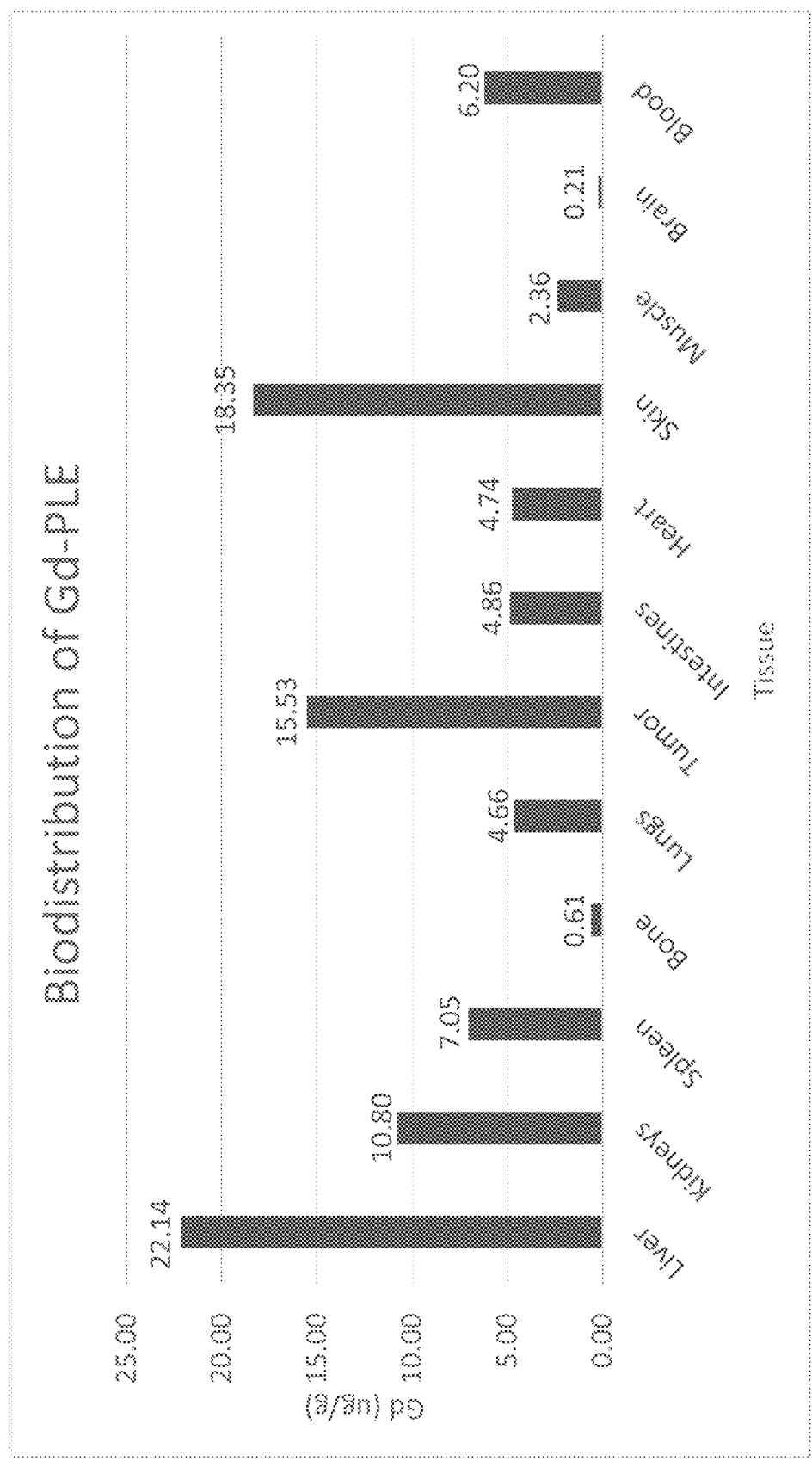
FIG. 16 is a bar graph showing tissue biodistribution of Gd-DO3A-404 in xenograft A549-flank bearing mice 72 hours post-administration. n=3 mice.

As seen in FIG. 16, the Gd-DO3A-404 was selectively taken up by tumor tissue, again demonstrating the suitability of the disclosed alkylphosphocholine analogs for targeted delivery to tumor tissue.

Example 10: Uptake of Gd-DO3A-404 in Triple-Negative Breast Cancer Model

In this example, we demonstrate the successful targeting of Gd-DO3A-404 to breast cancer tissue.

Figure 17:
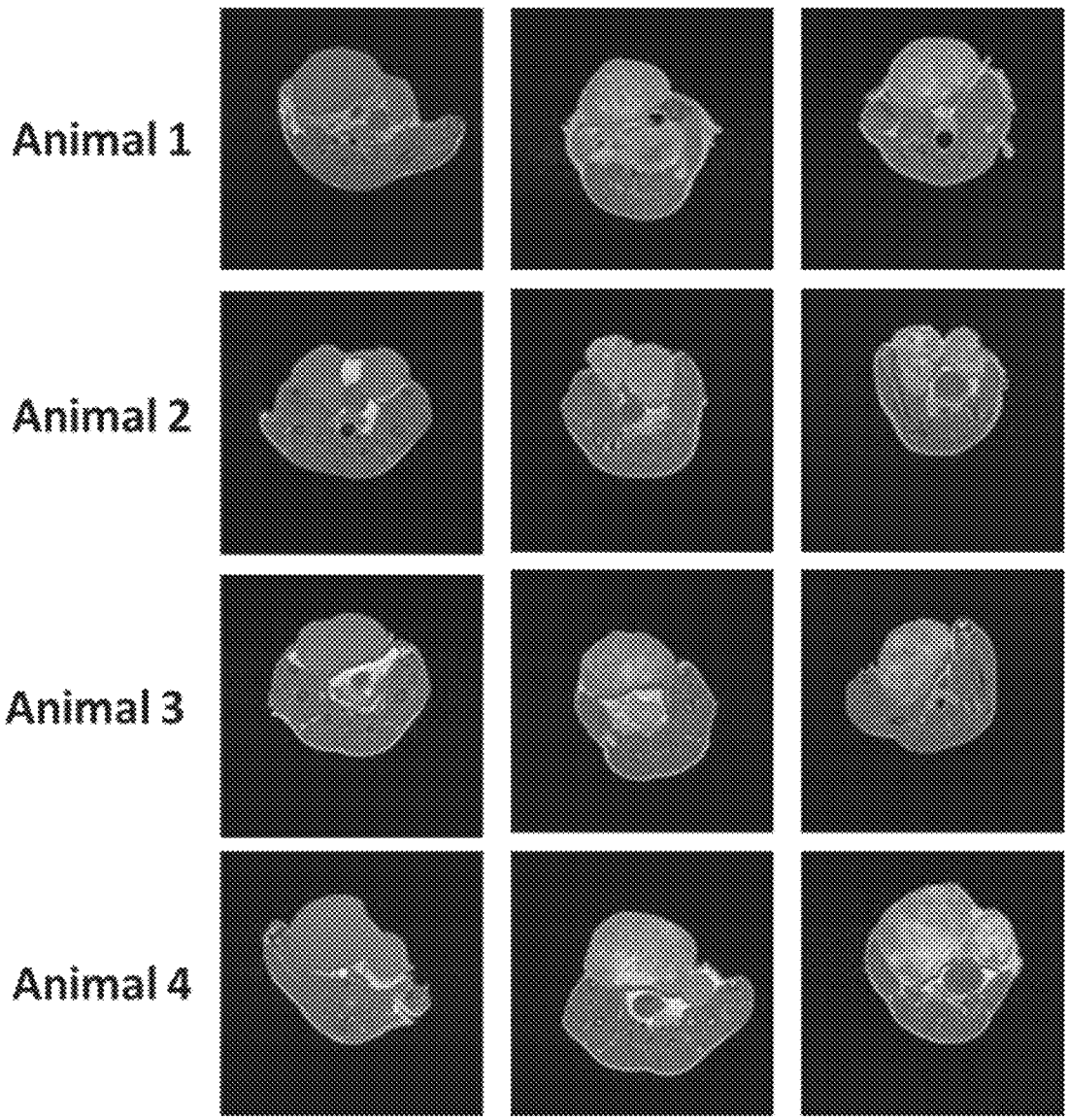
FIG. 17 shows time course MRI images obtained from a transgenic mouse triple-negative breast cancer model (n=4; Animals/rows 1-4). Alpha-beta crystalline overexpressing mice were imaged pre-administration (leftmost column) and 24 hours (center column) and 48 hours (rightmost column) post-administration.

Alpha-beta crystalline overexpressing mice (a triple negative breast cancer model) underwent MR imaging pre administration and 24 hours and 48 hours post-administration of Gd-DO3A-400 (n=4). As seen in FIG. 17, over 48 hours, the contrast agent was taken up by and localized to the breast cancer tissue.

This example illustrates that the disclosed alkylphosphocholine metal chelates can be used to target a wide range of solid tumor tissues.

Example 11: Uptake of Gd-DO3A-404 in Orthotopic Model

In this example, we demonstrate the successful targeting of Gd-DO3A-404 in two different orthotopic xenograft models.

Figure 18:
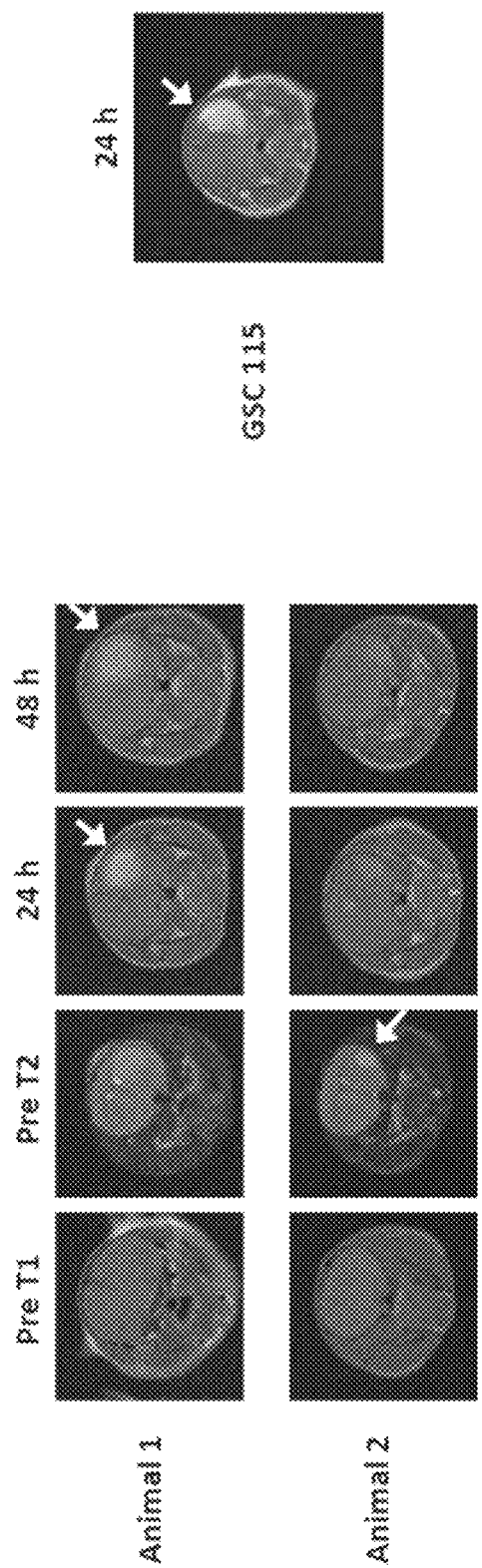
FIG. 18 shows $T_1$-weighted images obtained from orthotopic xenograft mouse models. NOD-SCID mice with orthotopic U87 xenografts were imaged pre-administration, 24 hours, and 48 hours post administration of Gd-DO3A-404 (left panel). Orthotopic GSC 115 was imaged at 24 hours post administration (right panel). GSC is a human glioma stem cell model which was isolated from a human glioma patient.

NOD-SCID mice with orthotopic U87 xenografts were imaged pre-administration, 24 hours, and 48 hours post administration of Gd-DO3A-404. As seen in FIG. 18 (left panel), the contrast agent was differentially taken up by the tumor tissue (see arrows).

Orthotopic GSC 115 was imaged at 24 hours post administration of Gd-DO3A-404. GSC is a human glioma stem cell model which was isolated from a human glioma patient. As seen in FIG. 18 (right panel), the contrast agent was differentially taken up by the tumor tissue (see arrow).

This example illustrates that the disclosed alkylphosphocholine metal chelates can be used to target a wide range of solid tumor tissues.

Example 12: Simultaneous PET/MR Imaging Demonstrating Tumor Targeting by Both Gd-DO3A-404 and $^{64}$Cu-DO3A-404

In this example, we demonstrate the successful use of both Gd-DO3A-404 and $^{64}$Cu-DO3A-404 as tumor targeting contrast agents (Gd-DO3A-404 for MRI and $^{64}$Cu-DO3A-404 for simultaneous PET imaging).

Simultaneous imaging was performed using a clinical Pet/MRI scanner. $^{64}$Cu-DO3A-404 has the same structure as Gd-DO3A-404, except that $^{64}$Cu, a positron emitting radionuclide, is chelated to the chelating moiety instead of Gd. $^{64}$Cu-DO3A-404 was synthesized (and can be synthesized using the methods disclosed herein; see, e.g., Example 1). Both the $^{64}$Cu-DO3A-404 and Gd-DO3A-404 chelates were injected simultaneously into a rat with a flank U87 (human glioma) xenograft.

Figure 19:
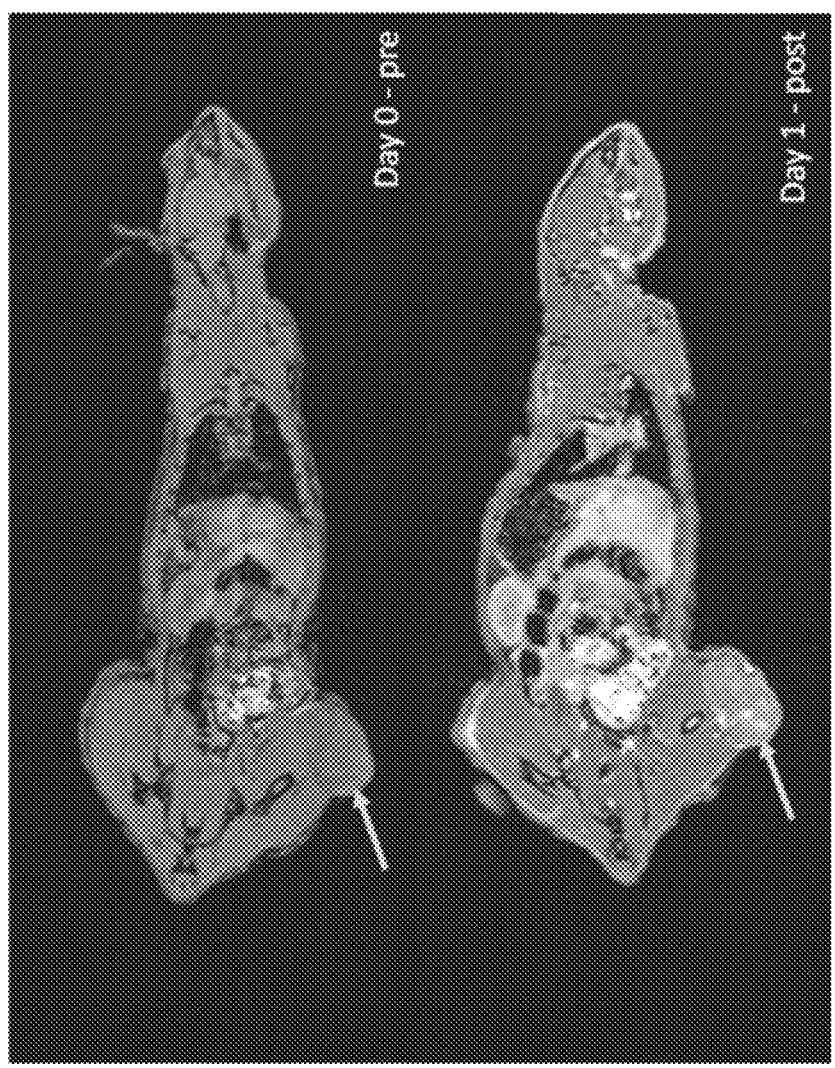
FIG. 19 shows $T_1$-weighted scans of a U87 flank xenograft bearing rat using a clinical 3.0 T PET/MR. Rats were imaged pre- and 24 hours post-administration of Gd-DO3A-404.

T1-weighted scans of the U87 flank xenograft were obtained using the clinical 3.0 T PET/MR. Rats were imaged pre- and 24 hours post-administration of the Gd-DO3A-404. The resulting MR images demonstrate selective tumor uptake of the Gd-DO3A-404 contrast agent (FIG. 19; arrow showing tumor location).

Figure 20:
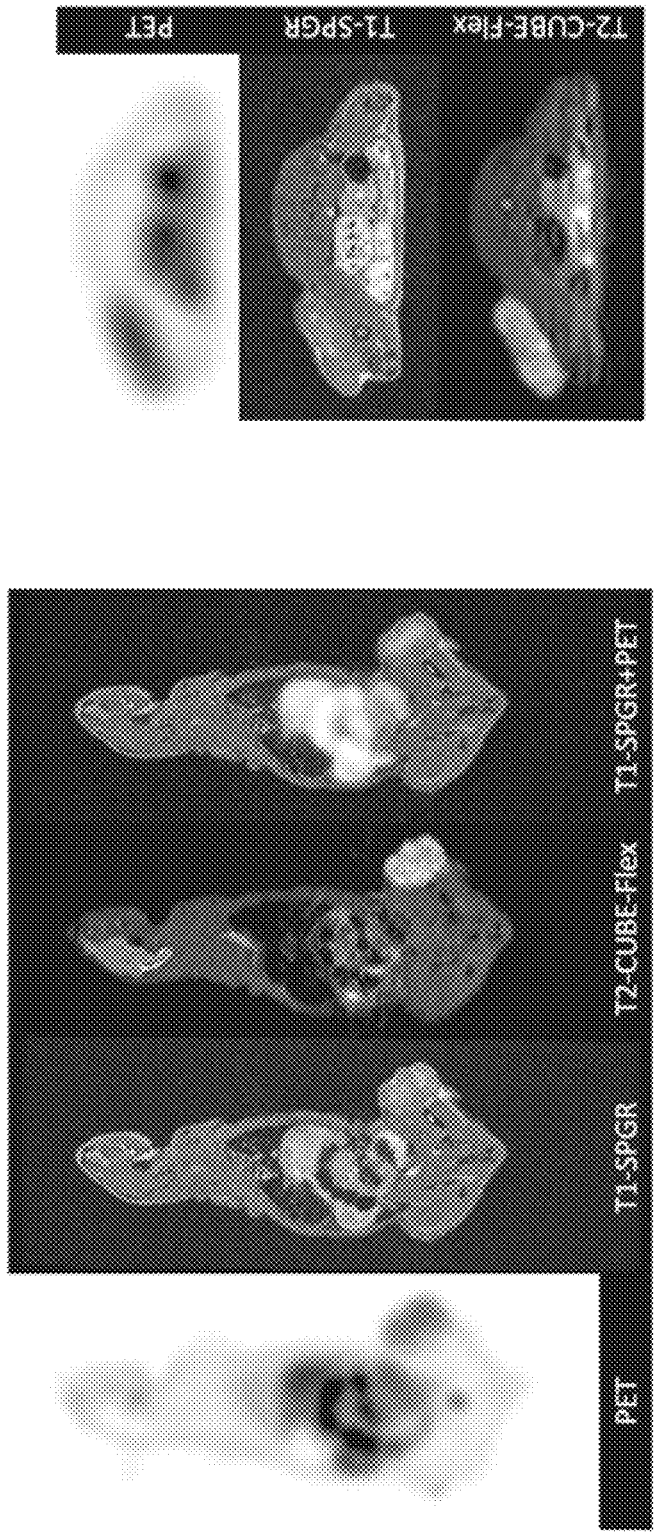
FIG. 20 shows simultaneous PET/MR images of a U87-flank bearing rat 24 hours post-administration of Gd-DO3A-404 and Cu-DO3A-404. Gd-DO3A-404 and $^{64}$Cu-DO3A-404 and were simultaneously administered to a U87-flank bearing rat. The rat was imaged using simultaneous PET/MR. Arrow points to tumor.

Simultaneous PET/MR scans of the U87-flank bearing rat 24 hours post-simultaneous administration of both Gd-DO3A-404 (the MRI contrast agent) and $^{64}$Cu-DO3A-404 (the PET contrast agent) were obtained. As seen in FIG. 20, fused T1-weighted MR and PET images showed excellent colocalization of contrast and activity in the flank and abdomen (arrow points to tumor). The tumor is enhanced enhances in both the T$_1$ and T2 MRI images (FIG. 20). Furthermore, the simultaneous PET scan demonstrates tumor uptake of the $^{64}$Cu-DO3A-404 PET contrast agent (FIG. 20), providing proof-of concept for using the disclosed chelates having a radioactive metal substituted for Gd in tumor imaging (such as PET imaging) and radiotherapy applications.

In sum, these examples demonstrate that gadolinium metal chelates that include an appropriate tumor-targeting phospholipid moiety, as disclosed herein, can be effective MRI contrast agents that demonstrate signal-enhancing uptake and retention in multiple cancer types. Such contrast agents will facilitate the detection, characterization, and staging of cancer and metastases with high spatial resolution. Furthermore, due to the high neutron capture cross-section of gadolinium, such agents may also have applications in targeted neutron capture therapy of cancer.

Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference. It is understood that the invention is not confined to the specific reagents, formulations, reaction conditions, etc., herein illustrated and described, but embraces such modified forms thereof as come within the scope of the following claims.

The invention claimed is:

1. A method of treating cancer in a subject, comprising:
   (a) contacting a biological sample that makes up part or all of the subject with a compound having the formula:

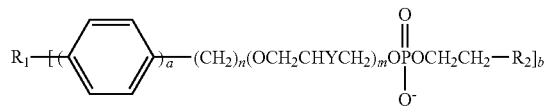

or a salt thereof, wherein:
R$_1$ comprises a chelating agent that is chelated to one or more gadolinium (Gd) atoms;
a is 0 or 1;
n is an integer from 12 to 30;
m is 0 or 1;
Y is selected from the group consisting of —H, —OH, —COOH, —COOX, —OCOX, and —OX, wherein X is an alkyl or an arylalkyl;
R$_2$ is selected from the group consisting of —N$^{+H}$$_3$, —N$^+$H$_2$Z, —N$^+$HZ$_2$, and —N$^+$Z$_3$, wherein each Z is independently an alkyl or an aroalkyl;
b is 1 or 2;
and wherein the chelating agent is selected from the group consisting of 1,4,7,10-tetraazacyclododecane-1,4,7-triacetic acid (DO3A) and its derivatives; 1,4,7-triazacyclononane-1,4-diacetic acid (NODA) and its derivatives; 1,4,7-triazacyclononane-1,4,7-triacetic acid (NOTA) and its derivatives; 1,4,7,10-tetraazacyclododecane-1,4,7,10-tetraacetic acid (DOTA) and its derivatives; 1,4,7-triazacyclononane, 1-glutaric acid-4,7-diacetic acid (NODAGA) and its derivatives; 1,4,7,10-tetraazacyclodecane, 1-glutaric acid-4,7,10-triacetic acid (DOTAGA) and its derivatives; 1,4,8,11-tetraazacyclotetradecane-1,4,8,11-tetraacetic acid (TETA) and its derivatives; 1,4,8,11-tetraazabicyclo[6.6.2]hexadecane-4,11-diacetic acid (CB-TE2A) and its derivatives; diethylene triamine pentaacetic acid (DTPA), its diester, and its derivatives; 2-cyclohexyl diethylene triamine pentaacetic acid (CHX-A"-DTPA) and its derivatives; deforoxamine (DFO) and its derivatives; 1,2-[[6-carboxypyridin-2-yl]methylamino]ethane (H$_2$dedpa) and its derivatives; and DADA and its derivatives, wherein DADA has the structure:

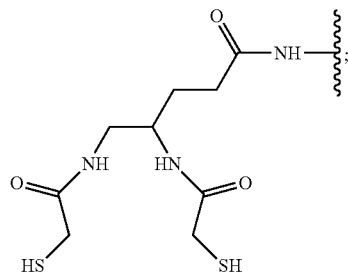 [SMILES: *NC(=O)CCC(CNC(=O)CS)NC(=O)CS]

(b) identifying individual cells or regions within the biological sample that are emitting signals characteristic of gadolinium; and
(c) directing an external radiotherapy beam to the identified individual cells or regions within the subject; whereby cancer is treated in the subject.

2. The method of claim 1, wherein the step of identifying individual cells or regions within the biological sample that are emitting signals characteristic of gadolinium is performed by magnetic resonance imaging (MRI).

3. The method of claim 1, wherein the subject is a human.

4. The method of claim 1, wherein the cancer that is treated is an adult solid tumor or a pediatric solid tumor.

5. The method of claim 4, wherein the cancer is selected from the group consisting of melanoma, neuroblastoma, lung cancer, adrenal cancer, colon cancer, colorectal cancer, ovarian cancer, prostate cancer, liver cancer, subcutaneous cancer, squamous cell cancer, intestinal cancer, retinoblastoma, cervical cancer, glioma, breast cancer, pancreatic cancer, Ewings sarcoma, rhabdomyosarcoma, osteosarcoma, retinoblastoma, Wilms' tumor, and pediatric brain tumors.

* * * * *